United States Patent
Butler

(10) Patent No.: US 11,514,577 B2
(45) Date of Patent: Nov. 29, 2022

(54) INTRINSIC CONTRAST OPTICAL CROSS-CORRELATED WAVELET ANGIOGRAPHY

(71) Applicant: William E. Butler, Boston, MA (US)

(72) Inventor: William E. Butler, Boston, MA (US)

(*) Notice: Subject to any disclaimer, the term of this patent is extended or adjusted under 35 U.S.C. 154(b) by 25 days.

(21) Appl. No.: 16/841,247

(22) Filed: Apr. 6, 2020

(65) Prior Publication Data

US 2020/0320710 A1    Oct. 8, 2020

Related U.S. Application Data

(60) Provisional application No. 62/829,290, filed on Apr. 4, 2019.

(51) Int. Cl.
 *G06K 9/00* (2022.01)
 *G06T 7/00* (2017.01)
 (Continued)

(52) U.S. Cl.
 CPC ........ *G06T 7/0016* (2013.01); *A61B 5/02416* (2013.01); *A61B 5/726* (2013.01);
 (Continued)

(58) Field of Classification Search
 CPC ................. G06T 7/0016; G06T 5/20; G06T 2207/10121; G06T 2207/20064;
 (Continued)

(56) References Cited

U.S. PATENT DOCUMENTS 3,335,716 A    8/1967  Alt et al.
5,628,980 A    5/1997  Ranganathan et al.
(Continued)

FOREIGN PATENT DOCUMENTS

CN    101406392 B    5/2011
EP    1322219 B1    5/2007
(Continued)

OTHER PUBLICATIONS

Butler, W.E., "Wavelet brain angiography suggests arteriovenous pulse wave phase locking," PLOS One, vol. 12, No. 11, Nov. 15, 2017 (16 pages).

(Continued)

*Primary Examiner* — Atiba O Fitzpatrick
(74) *Attorney, Agent, or Firm* — Edell, Shapiro & Finnan, LLC

(57) ABSTRACT

A time sequenced series of optical images of a patient is obtained at a rate faster than cardiac frequency, wherein the time sequenced series of images capture one or more physical properties of intrinsic contrast. A cross-correland signal from the patient is obtained. A cross-correlated wavelet transform analysis is applied to the time sequenced series of optical images to yield a spatiotemporal representation of cardiac frequency phenomena. The cross-correlated wavelet transform analysis comprises performing a wavelet transform on the time-sequenced series of optical images to obtain a wavelet transformed signal, cross-correlating the wavelet transformed signal with the cross-correland signal to obtain a cross-correlated signal, filtering the cross-correlated signal at cardiac frequency to obtain a filtered signal, and performing an inverse wavelet transform on the filtered signal to obtain a spatiotemporal representation of the time sequenced series of optical images. Images of the cardiac frequency phenomena are generated.

20 Claims, 7 Drawing Sheets

(51) Int. Cl.
*A61B 6/00* (2006.01)
*A61B 5/00* (2006.01)
*A61B 5/024* (2006.01)
*G06T 5/20* (2006.01)

(52) U.S. Cl.
CPC ............ *A61B 6/504* (2013.01); *A61B 6/5217* (2013.01); *G06T 5/20* (2013.01); *G06T 2207/10121* (2013.01); *G06T 2207/20064* (2013.01); *G06T 2207/30104* (2013.01)

(58) Field of Classification Search
CPC ...... G06T 2207/30104; A61B 5/02416; A61B 5/726; A61B 6/504; A61B 6/5217
See application file for complete search history.

(56) References Cited

U.S. PATENT DOCUMENTS

| | | | |
|---|---|---|---|
| 5,637,871 | A | 6/1997 | Piety et al. |
| 5,963,676 | A | 10/1999 | Wu et al. |
| 6,195,456 | B1 | 2/2001 | Balasubramanian et al. |
| 6,442,414 | B1 | 8/2002 | Watanabe |
| 6,549,801 | B1 | 4/2003 | Chen et al. |
| 6,842,638 | B1 | 1/2005 | Suri et al. |
| 6,975,753 | B2 | 12/2005 | Matsuura et al. |
| 6,985,632 | B2 | 1/2006 | Sato et al. |
| 7,020,314 | B1 | 3/2006 | Suri et al. |
| 7,035,679 | B2 | 4/2006 | Addison et al. |
| 7,201,892 | B2 | 4/2007 | Achilefu et al. |
| 7,359,062 | B2 | 4/2008 | Chen et al. |
| 7,602,183 | B2 | 10/2009 | Lustig et al. |
| 8,244,334 | B2 | 8/2012 | Huang et al. |
| 8,306,295 | B2 | 11/2012 | Bruder et al. |
| 8,306,303 | B2 | 11/2012 | Bruder et al. |
| 8,417,048 | B2 | 4/2013 | Reboni et al. |
| 8,559,692 | B2 | 10/2013 | Reboni et al. |
| 8,605,976 | B2 | 12/2013 | Diamant et al. |
| 8,611,633 | B2 | 12/2013 | Kwon et al. |
| 8,628,751 | B2 | 1/2014 | Neumann et al. |
| 8,948,480 | B2 | 2/2015 | Liu et al. |
| 9,019,305 | B2 | 4/2015 | Baumgart et al. |
| 9,036,780 | B2 | 5/2015 | Kyriakou et al. |
| 9,165,349 | B2 | 10/2015 | Kwon et al. |
| 9,324,005 | B2 | 4/2016 | Wadhwa et al. |
| 9,345,413 | B2 | 5/2016 | Schie et al. |
| 9,357,916 | B2 | 6/2016 | Srivastava et al. |
| 9,811,901 | B2 | 11/2017 | Wu et al. |
| 9,814,384 | B2 | 11/2017 | Schmoll |
| 9,836,849 | B2 | 12/2017 | Dickrell, III et al. |
| 10,123,761 | B2 | 11/2018 | Butler |
| 10,226,176 | B2 | 3/2019 | Schmoll |
| 10,299,677 | B2 | 5/2019 | Spaide |
| 10,653,379 | B2 | 5/2020 | Rapoport |
| 2004/0101090 | A1 | 5/2004 | Drummond et al. |
| 2005/0080327 | A1 | 4/2005 | Jenkins et al. |
| 2007/0106146 | A1 | 5/2007 | Altmann et al. |
| 2007/0106149 | A1 | 5/2007 | Mistretta |
| 2007/0185393 | A1 | 8/2007 | Zhou et al. |
| 2008/0045847 | A1* | 2/2008 | Farag ................ A61B 5/02055 600/500 |
| 2008/0226149 | A1 | 9/2008 | Wischmann et al. |
| 2010/0113949 | A1 | 5/2010 | Sathyanarayana |
| 2010/0272184 | A1 | 10/2010 | Fishbain et al. |
| 2011/0142288 | A1 | 6/2011 | Diamant et al. |
| 2012/0134553 | A1 | 5/2012 | Liao et al. |
| 2013/0101187 | A1 | 4/2013 | Sundar et al. |
| 2013/0116554 | A1 | 5/2013 | Kaiser et al. |
| 2013/0243348 | A1 | 9/2013 | Goshen et al. |
| 2014/0005563 | A1 | 1/2014 | Ramanathan et al. |
| 2014/0044330 | A1 | 2/2014 | Klingenbeck |
| 2014/0072190 | A1 | 3/2014 | Wu et al. |
| 2014/0072228 | A1 | 3/2014 | Rubinstein et al. |
| 2014/0072229 | A1 | 3/2014 | Wadhwa et al. |
| 2014/0378795 | A1 | 12/2014 | McKenna |
| 2015/0045684 | A1 | 2/2015 | Schie |
| 2015/0190533 | A1 | 7/2015 | Newton et al. |
| 2015/0257653 | A1 | 9/2015 | Hyde et al. |
| 2016/0135775 | A1 | 5/2016 | Mistretta et al. |
| 2016/0189394 | A1 | 6/2016 | Zhang et al. |
| 2016/0220112 | A1 | 8/2016 | Schmoll |
| 2016/0267704 | A1 | 9/2016 | Mistretta et al. |
| 2016/0349346 | A1 | 12/2016 | Cheng |
| 2017/0000441 | A1 | 1/2017 | Butler |
| 2017/0367603 | A1 | 12/2017 | Spector |
| 2018/0047160 | A1 | 2/2018 | Wu et al. |
| 2018/0055471 | A1 | 3/2018 | Redel |
| 2019/0015061 | A1 | 1/2019 | Liebeskind et al. |
| 2019/0046147 | A1 | 2/2019 | Butler |
| 2019/0053780 | A1* | 2/2019 | Song ................ A61B 8/5269 |
| 2019/0159707 | A1 | 5/2019 | Albuquerque et al. |
| 2019/0343383 | A1 | 11/2019 | Spaide |
| 2020/0193597 | A1* | 6/2020 | Fan ................ G16H 30/40 |
| 2020/0245961 | A1 | 8/2020 | Butler |
| 2020/0245965 | A1 | 8/2020 | Butler |
| 2020/0286237 | A1 | 9/2020 | Butler |
| 2020/0305822 | A1 | 10/2020 | Butler |
| 2020/0397396 | A1 | 12/2020 | Butler |
| 2021/0137634 | A1 | 5/2021 | Lang |

FOREIGN PATENT DOCUMENTS

| | | |
|---|---|---|
| WO | 2020163614 A1 | 8/2020 |
| WO | 2020163629 A1 | 8/2020 |
| WO | 2020185706 A1 | 9/2020 |
| WO | 2020198592 A1 | 10/2020 |
| WO | 2020206430 A1 | 10/2020 |

OTHER PUBLICATIONS

Hyvärinen, L., et al., "Indocyanine green fluorescence angiography." Acta ophthalmologica, vol. 58, No. 4, pp. 528-538, 1980 (11 pages).

Desmettre, T., et al., "Fluorescence properties and metabolic features of indocyanine green (ICG) as related to angiography," Survey of ophthalmology, vol. 45, No. 1, pp. 15-27, Jul. 2000 (13 pages).

Kuroiwa, T et al., "Development and clinical application of near-infrared surgical microscope: preliminary report," Minimally Invasive Neurosurgery, vol. 44, No. 4, pp. 240-242, 2001. Abstract accessed online on Jun. 16, 2020 at: <http://www.thieme-connect.de/DOI/DOI?10.1055/s-2001-19929> (2 pages).

Mourant, J. et al., "Hemoglobin parameters from diffuse reflectance data," Journal of Biomedical Optics, vol. 19, No. 3, p. 037004, 2014 (10 pages).

Robles, E., et al., "Assessing hemoglobin concentration using spectroscopic optical coherence tomography for feasibility of tissue diagnostics," Biomedical Optics Express, vol. 1, No. 1, p. 310, 2010 (8 pages).

Lahiri, B., et al., "Medical applications of infrared thermography: A review," Infrared Physics & Technology, vol. 55, No. 4, pp. 221-235, Jul. 2012 (16 pages).

Bachmann, L. et al., "Fluorescence Spectroscopy of Biological Tissues: A Review," Applied Spectroscopy Reviews, vol. 41, No. 6, pp. 575-590, Jul. 2006 (16 pages).

Devor, A., et al., "Frontiers in optical imaging of cerebral blood flow and metabolism," Journal of Cerebral Blood Flow and Metabolism, vol. 32, No. 7, pp. 1259-1276, Jan. 18, 2012 (18 pages).

Chen, Z., et al., "Optical Doppler tomography," IEEE Journal on Selected Topics in Quantum Electronics, vol. 5, No. 4, pp. 1134-1142, Jul. 1, 1999 (10 pages).

Yazdanfar, S., et al., "High resolution imaging of in vivo cardiac dynamics using color Doppler optical coherence tomography," Optics Express, vol. 1, No. 13, pp. 424-431, Dec. 22, 1997 (8 pages).

Chen, C., et al., "Optical coherence tomography based angiography [Invited]," Biomedical Optics Express, vol. 8, No. 2, p. 1056, Jan. 24, 2017 (27 pages).

Makita, S., et al., "Optical coherence angiography," Optics Express, vol. 14, No. 17, pp. 114-116, Aug. 21, 2006 (20 pages).

Zhao, Y., et al., "Phase-resolved optical coherence tomography and optical Doppler tomography for imaging blood flow in human skin

(56) References Cited

OTHER PUBLICATIONS with fast scanning speed and high velocity sensitivity," Optics Letters, vol. 25, No. 2, pp. 114-116, Jan. 15, 2000 (4 pages).
Chen, Z., et al., "Noninvasive imaging of in vivo blood flow velocity using optical Doppler tomography," Optics Letters, vol. 22, No. 14, Jul. 15, 1997 (3 pages).
Izatt, J., et al., "In vivo bidirectional color Doppler flow imaging of picoliter blood volumes using optical coherence tomography," Optics Letters, vol. 22, No. 18, Sep. 15, 1997 (3 pages).
Drexler, W., "Ultrahigh-resolution optical coherence tomography," Journal of Biomedical Optics 9(1), 47-74, Jan./Feb. 2004 (28 pages).
Wang, R., et al., "Phase-sensitive optical coherence elastography for mapping tissue microstrains in real time," Applied Physics Letters, vol. 90, No. 16, Apr. 19, 2007 (4 pages).
Wu, H., et al., "Eulerian Video Magnification for Revealing Subtle Changes in the World," Association for Computing Machinery, vol. 31, No. 4, pp. 1-8, Jul. 2012 (9 pages).
International Search Report and Written Opinion received in international application No. PCT/US20/26886, dated Jun. 23, 2020 (15 pages).
Medda et al., A wavelet clustering technique for the identification of functionally connected regions in the rat brain using resting state fMRI, IEEE Statistical Signal Processing Workshop (SSP), Aug. 2012, pp. 424-427.
Mizuno-Matsumoto et al., Wavelet-crosscorrelation analysis: Nonstationary analysis of neurophysiological signals, Brain Topography, 2005, vol. 17, No. 4, pp. 237-252.
Morlet et al, Wave propagation and sampling theory—part I: Complex signal and scattering in multilayered media, Geophysics, Feb. 1982, vol. 47, No. 2, pp. 203-221.
Najmi et al., The continuous wavelet transform and variable resolution time-frequency analysis, Johns Hopkins Apl Technical Digest, 1997, vol. 18, No. 1, pp. 134-140.
Schultze-Kraft et al., Exploiting the potential of three dimensional spatial wavelet analysis to explore nesting of temporal oscillations and spatial variance in simulateous EEG-fMRI data, Progress in Biophysics and Molecular Biology, Mar. 2011, vol. 105(1-2), pp. 67-79.
Serroukh, Wavelet coefficients cross-correlation analysis of times series, Electronic Journal of Applied Statistical Analysis, 2012, vol. 5, iss. 2, pp. 289-296.
Shannon, Communication in the Presence of Noise, Proceedings of the IEEE, Feb. 1998, vol. 86, iss. 2, pp. 447-457.
Hardesty et al., Safety, efficacy, and cost of intraoperative indocyanine green angiography compared to intraoperative catheter angiography in cerebral aneurysm surgery, Journal of clinical neuroscience, Apr. 2014, pp. 1-6.
Hyvarinen et al., Indocyanine green fluorescence angiography, Acta Ophthalmologica, Aug. 1980, vol. 58(4), pp. 528-538.
Aaslid et al., Noninvasive transcranial doppler ultrasound recording of flow velocity in basal cerebral arteries, J Neurosurg, 1982, vol. 57(6), pp. 769-774.
Vo et al., Vonn distribution of relative phase for statistical image modeling in complex wavelet domain, Signal Processing, 2011, vol. 91(1), pp. 114-125.
Abramovich et al., Wavelet Analysis and Its Statistical Applications, Journal of the Royal Statistical Society Series D (The Statistician), 2000, vol. 49(1), pp. 1-29.
Kim et al., Cine MR CSF flow study in hydrocephalus: what are the valuable parameters? Acta neurochirurgica Supplement, 1998, vol. 71(6), pp. 343-346.
Kulkarni et al., Endoscopic third ventriculostomy in the treatment of childhood hydrocephalus, The Journal of Pediatrics, Aug. 2009, vol. 155, No. 2, pp. 254-259.
Meairs et al., Ultrasound, microbubbles and the blood-brain barrier, Progress in Biophysics & Molecular Biology, Apr. 2007, vol. 93(1-3), pp. 354-362.
Saikali et al., A three-dimensional digital segmented and deformable brain atlas of the domestic pig, Journal of Neuroscience Methods, Sep. 2010, vol. 192(1), pp. 102-109.
Wilson, Monro-Kellie 2.0: The dynamic vascular and venous pathophysiological components of intracranial pressure, Journal of Cerebral Blood Flow & Metabolism, May 2016, vol. 36(8), pp. 1338-1350.
Bernstein et al., Handbook of MRI Pulse Sequences, Elsevier Academic Press, 2004, pp. 443-454.
Kim et al., Phase-shift between arterial flow and ICP pulse during infusion test, Acta Neurochirurgica, Feb. 3, 2015, vol. 157(4), pp. 633-638.
Kawoos et al., Advances in Intracranial Pressure Monitoring and Its Significance in Managing Traumatic Brain Injury, International Journal of Molecular Sciences, 2015, vol. 16 (12), pp. 28979-28997.
Gabor, Theory of communication. Part 2: The analysis of hearing, Journal of the Institution of Electrical Engineers—Part III: Radio and Communication Engineering, 1946, vol. 93(26), pp. 442-445.
Goriely et al., Mechanics of the brain: perspectives, challenges, and opportunities, Biomechanics and modeling in mechanobiology, Feb. 26, 2015, vol. 14(5), pp. 931-965.
Helbok et al., Intracranial Pressure and Cerebral Perfusion Pressure Monitoring in Non-TBI Patients: Special Considerations, Neurocritical Care, 2014, vol. 21(S2), pp. S85-S94 (published online, Sep. 11, 2014, 10 pages).
Balestreri et al., Intracranial hypertension: what additional information can be derived from ICP waveform after head injury?, Acta Neurochirurgica (wien), 2004, vol. 146(2), pp. 131-141.
Carrera et al., What Shapes Pulse Amplitude of Intracranial Pressure?, Journal of Neurotrauma, Feb. 2010, vol. 27(2), pp. 317-324.
Bangare et al., Reviewing Otsu's method for image thresholding, International Journal of Applied Engineering Research, 2015, vol. 10, No. 9, pp. 21777-21783.
Bhadelia et al., Analysis of cerebrospinal fluid flow waveforms with gated phase-contrast MR velocity measurements, American Journal of Neuroradiology, Feb. 1995, vol. 16(2), pp. 389-400.
Bonnefous et al., Quantification of arterial flow using digital subtraction angiography, Medical Physics, Oct. 2012, vol. 39, iss. 10, pp. 6264-6275.
Chang et al., Emerging techniques for evaluation of the hemodynamics of intracranial vascular pathology, The Neuroradiology Journal, Feb. 2015, vol. 28(1), pp. 19-27.
Dawkins et al., Complications of cerebral angiography: A prospective analysis of 2,924 consecutive procedures, Neuroradiology, Aug. 2007, vol. 49, iss. 9, pp. 753-759.
Torrence et al., A Practical Guide to Wavelet Analysis, Bulletin of the American Meteorological Society, Jan. 1998, vol. 79, iss. 1, pp. 61-78.
Zou et al., Increased Phase Synchronization between Intracranial Pressure and Arterial Blood Pressure during Elevated Intracranial Pressure in Dogs, Proceedings of the 2005 IEEE, Engineering in Medicine and Biology 27th Annual Conference, Shanghai, China, Sep. 1-4, 2005, pp. 315-318.
Unekawa et al., RBC velocities in single capillaries of mouse and rat brains are the same, despite 10-fold difference in body size, Brain Research, 2010, vol. 1320, pp. 69-73.
Grinsted et al., Application of the cross wavelet transform and wavelet coherence to geophysical time series, Nonlinear Processes in Geophysics, 2004, vol. 11, pp. 561-566.
Grist et al., Time-Resolved Angiography: Past, Present, and Future, Journal of Magnetic Resonance Imaging, 2012, vol. 36(6), pp. 1273-1286.
Jiang et al., Computational Fluid Dynamics Simulations of Intracranial Aneurysms at Varying Heart Rates: A "Patient-Specific" Study, Journal of Biomechanical Engineering, Sep. 2009, vol. 131(9), pp. 09100-1-09100-11.
Kachelriess et al., ECG-correlated image reconstruction from subsecond multi-slice spiral CT scans of the heart, Medical Physics, 2000, vol. 27(12), pp. 1881-1902.
Kirk et al., Phase-only complex-valued spatial filter, Journal of the Optical Society of America, Aug. 1971, vol. 61, iss. 8, pp. 1023-1028.

(56) References Cited

OTHER PUBLICATIONS

Latka et al., Phase dynamics in cerebral autoregulation, American journal of physiology, heart and circulatory physiology, 2005, vol. 289(5), pp. H2272-H2279.
Shpilfoygel et al., X-ray videodensitometric methods for blood flow and velocity measurement: A critical review of literature, Medical Physics, Sep. 2000, vol. 27, iss. 9, pp. 2008-2023.
Mistretta, Sub-Nyquist acquisition and constrained reconstruction in time resolved angiography, Medical Physics, 2011, vol. 38, iss. 6, pp. 2975-2985.
Peng et al., Wavelet phase synchronization analysis of cerebral blood flow autoregulation, IEEE Transactions on Biomedical Engineering, Apr. 2010, vol. 57, No. 4, pp. 960-968.
Pereira et al., A DSA-based method using contrast motion estimation for the assessment of the intra-aneurysmal flow changes induced by flow-diverter stents, American Journal of Neuroradiology, Apr. 2013, vol. 34(4), pp. 808-815.
Wikipedia article entitled "Band-pass filter", <https://en.wikipedia.org/wiki/Band-pass_filter>, last edited on Feb. 25, 2020, accessed on Mar. 26, 2020 (4 pages).
YouTube video, "Eulerian Video Magnification" accessed online on Jun. 15, 2020 at: <https://www.youtube.com/watch?v=ONZcjs1Pjmk>, published May 23, 2012 (2 pages).
U.S. Appl. No. 62/824,582 Entitled Device and Method for Reconstructing Cardiac Frequency Phenomena in Angiographic Data, filed Mar. 27, 2019 (25 pages).
Bracewell, R. N., "Two-Dimensional Imaging", Prentice Hall, chapters 4-7, 12, and 15, 1995 (pp. 1-100 of 206 pages).
Bracewell, R. N., "Two-Dimensional Imaging", Prentice Hall, chapters 4-7, 12, and 15, 1995 (pp. 101-206 of 206 pages).
Des Plantes, "Eine Neue Methode Zur Differenzierung in der Rontgenographie (Planigraphies)," Acta Radiologica, 13:2, 182-192, 1932 (16 pages).
Tuy, H. K., "An Inversion Formula for Cone-Beam Reconstruction," SIAM Journal on Applied Mathematics, 43 (3):546-552, 1983 (7 pages).
Wikipedia article "Dose Area Product" accessed online on Jun. 15, 2020 at: <https://en.wikipedia.org/wiki/Dose_area_product> (2 pages).
Anonymous, ArtisZeego, Data Sheet VC21, Multi-axis for interventional imaging, Oct. 2014, 36 pages, www.siemens.com/healthcare.
Babin et al., Segmentation and length measurement of the abdominal blood vessels in 3-D MRI images, Conference Proceedings IEEE Engineering in Medicine and Biology Society, Sep. 2-6, 2009, pp. 4399-4402.
Barfett et al., Intra-vascular blood velocity and volumetric flow rate calculated from dynamic 4D CT angiography using a time of flight technique, The International Journal of Cardiovascular Imaging, Oct. 2014, vol. 30(7), pp. 1383-1392.
Bhadelia et al., Cerebrospinal fluid pulsation amplitude and its quantitative relationship to cerebral blood flow pulsations: a phase-contrast MR flow imaging study, Neuroradiology, Apr. 1997, vol. 39(4), pp. 258-264.
Long et al., Spatiotemporal wavelet analysis for functional MRI, NeuroImage, Oct. 2004, vol. 23(2), pp. 500-516.
Daubechies, The wavelet transform, time-frequency localization, and signal analysis, IEEE Transactions on Information Theory, Sep. 1990, vol. 36, iss. 5, pp. 961-1005.
Gabor, Theory of communication. Part I: The analysis of information, Journal of the Institution of Electrical Engineers—Part III: Radio and Communication Engineering, Nov. 1946, vol. 93(26), pp. 429-441.
Goupillaud et al., Cycle-octave and related transforms in seismic signal analysis, Geoexploration, Oct. 1984, vol. 23, iss. 1, pp. 85-102.
Kuroiwa et al., Development and clinical application of near-infrared surgical microscope: preliminary report, Minimally invasive neurosurgery: MIN, Dec. 2001, vol. 44(4), pp. 240-242.
Markl et al., 4D Flow MRI, Journal of Magnetic Resonance Imaging (JMRI), Oct. 2012, vol. 36, iss. 5, pp. 1015-1036.
Moser et al., On the accuracy of EPI-based phase contrast velocimetry, Magnetic Resonance Imaging, Nov. 2000, vol. 18, iss. 9, pp. 1115-1123.
Nyquist et al., Certain topics in telegraph transmission theory, Transactions of the American Institute of Electrical Engineers, Feb. 1928, vol. 47, iss. 2, pp. 617-644.
Persson et al., Hydrocephalus prevalence and outcome in a population-based cohort of children born in 1989-1998, Acta Paediatrica, Jun. 2005, vol. 94, iss 6, pp. 726-732.
Provost et al., 3D Ultrafast ultrasound imaging in vivo, Physics in Medicine and Biology, Sep. 10, 2014, vol. 59, iss. 19, L1-L13.
Raabe et al., Prospective evaluation of surgical microscope-integrated intraoperative near-infrared indocyanine green videoangiography during aneuryism surgery, Journal of Neurosurgery, Dec. 2005, vol. 103, iss. 6, pp. 982-989.
Rao et al., Shear strain imaging using shear deformations, Med Phys., Feb. 2008, vol. 35(2), pp. 412-423.
Rasul et al., Is endoscopic third ventriculostomy superior to shunts in patients with non-communicating hydrocephalus? A systematic review and meta-analysis of the evidence, Acta Neurochirurgica, May 2013, vol. 155, iss. 5, pp. 883-889.
Sugawara et al., Arterial path length measurements required for the pulse wave velocity, Journal of Hypertension, May 2009, vol. 27, iss. 5, pp. 1102-1104.
Tomita et al., Automated method for tracking vast numbers of FITC-labeled RBCs in microvessels of rat brain in vivo using a high-speed confocal microscope system, Microcirculation, Feb. 2008, vol. 15, iss. 2, pp. 163-174.
Unser, Sampling—50 years after Shannon, Proceedings of the IEEE, Apr. 2000, vol. 88, No. 4, pp. 569-587.
Wagshul et al., The pulsating brain: A review of experimental and clinical studies of intracranial pulsatility, Fluids and Barriers of the CNS, Jan. 18, 2011, vol. 8, iss. 5, pp. 1-23.
Weaver et al., Brain mechanical property measurement using MRE with intrinsic activation, Physics in Medicine Biology, Nov. 2012, vol. 57, No. 22, pp. 7275-7287.
Zaidi et al., Indocyanine Green Angiography in the Surgical Management of Cerebral Arteriovenous Malformations: Lessons Learned in 130 Consecutive Cases, Operative Neurosurgery, Jun. 2014, vol. 10, No. 2, pp. 246-251.
Zou et al., Intracranial pressure waves: characterization of a pulsation absorber with notch filter properties using systems analysis, J. Neurosurg Pediatrics, Jul. 2008, vol. 2(1), pp. 83-94.
Henneman et al., Phase analysis of gated myocardial perfusion single-photon emission computed tomography compared with tissue doppler imaging for the assessment of left ventricular dyssynchrony, Journal of the American College of Cardiology, Apr. 2007, vol. 49 (16), pp. 1708-1714.
Kingdom et al., Sensitivity to contrast histogram differences in synthetic wavelet-textures, Vision Research, Mar. 2001, vol. 41(5), pp. 585-598.
Li et al., Cross-frequency coupling during isoflurane anaesthesia as revealed by electroencephalographic harmonic wavelet bicoherence, Neurosciences and Neuroanaesthesia, British Journal of Anaesthesia, Mar. 2013, vol. 110(3), pp. 409-419.
Moore, A modification of the Rayleigh test for vector data, Biometrika, Apr. 1980, vol. 67(1), pp. 175-180.
Mousavi et al., A wavelet transform based method to determine depth of anesthesia to prevent awareness during general anesthesia, Computational and Mathematical Methods in Medicine, 2014, vol. 2014, pp. 1-13.
Rakhmanov et al., A cross-correlation method for burst searches with networks of misaligned gravitational-wave detectors, Institute of Physics Publishing, Classical and Quantum Gravity, Sep. 6, 2005, vol. 22(18), pp. S1311-S1320.
Wang et al., The residual phase estimation of a seismic wavelet using a renyi divergence-based criterion, Journal of Applied Geophysics, Jul. 2014, vol. 106, pp. 96-105.
Yu, Histogram Matching Seismic Wavelet Phase Estimation, May 2012, Masters thesis, University of Houston.
Anor et al., Modeling of blood flow in arterial trees, Focus Article, WIREs Systems Biology and Medicine, Sep./Oct. 2010, vol. 2, pp. 612-623.

(56) References Cited

OTHER PUBLICATIONS

Hamberg et al., Quantitative high-resolution measurement of cerebrovascular physiology with slip-ring CT, AJNR Am J Neuroradiol, Apr. 1996, vol. 17(4), pp. 639-650.
Kashif et al., Model-based non-invasive estimation of intracranial pressure from cerebral blood flow velocity and arterial pressure, Science Translational Medicine, Apr. 2012, vol. 4(129): 129ra44.
Lassen et al., Tracer Kinetic Methods in Medical Physiology, 1979, Raven Press, New York.
Linninger et al., A mathematical model of blood, cerebrospinal fluid and brain dynamics, J Mathematical Biology, Dec. 2009, vol. 59(6), pp. 729-759.
Bayer et al., Two-dimensional simulations of displacement accumulation incorporating shear strain, Ultrason Imaging, Jan. 2014, vol. 36(1), pp. 55-73.
Braun et al., High-resolution mechanical imaging of the human brain by three-dimensional multifrequency magnetic resonance elastography at 7T, NeuroImage, Apr. 2014, vol. 90, pp. 308-314.
Feingold et al., Quantitative volumetric perfusion mapping of the microvasculature using contrast ultrasound, Invest Radiol, Oct. 2010, vol. 45(10), pp. 669-674.
Gauthier et al., Assessment of quantitative perfusion parameters by dynamic contrast-enhanced sonography using a deconvolution method, an in vitro and in vivo study, J Ultrasound Med, Apr. 2012, vol. 31(4), pp. 595-608.
Johnson et al., Local mechanical properties of white matter structures in the human brain, NeuroImage, Oct. 2013, vol. 79, pp. 145-152.
Ashmead, Morelet Wavelets in quantum mechanics, Quanta, Nov. 2012, vol. 1, Issue 1, pp. 58-70.
Johnstone et al., Wavelet threshold estimators for data with correlated noise, Journal of the Royal Statistical Society: Series B (Statistical Methodology), 1997, 59(2), pp. 319-351.
Khullar et al., Wavelet-based fMRI analysis: 3-d denoising, signal separation, and validation metrics, NeuroImage, Feb. 2011, vol. 54(4), pp. 2867-2884.
Martin J. Murphy, "Tracking Moving Organs in Real Time", Seminars in Radiation Oncology, vol. 14, No. 1, Jan. 2004, pp. 91-100.
Frangi et al., "Multiscale Vessel Enhancement Filtering," Medical Image Computing and Computer-Assisted Intervention—MICCAI'98, Lecture Notes in Computer Science, vol. 1496, Springer Verlag, Berlin, Germany, pp. 130-137, 1998 (8 pages).
Ashmead, John, "Morlet Wavelets in Quantum Mechanics," Quanta, vol. 1, issue 1, Nov. 2012, pp. 58-70 (13 pages).
Baker et al., "Lucas-Kanade 20 Years On: A Unifying Framework," International Journal of Computer Vision 56(3), 221-255, 2004 (35 pages).
Balakrishnan et al., "VoxelMorph: A Learning Framework for Deformable Medical Image Registration," arXiv:1809.05231 [cs.CV], Sep. 1, 2019 (16 pages).
Bao et al., "Depth-Aware Video Frame Interpolation," IEEE Conference on Computer Vision and Pattern Recognition, pp. 3703-3712, 2019 (10 pages).
Butler, William E., "Wavelet brain angiography suggests arteriovenous pulse wave phase locking," Plos One, Nov. 15, 2017 (23 pages).
Chen et al., "A Labeling-Free Approach to Supervising Deep Neural Networks for Retinal Blood Vessel Segmentation," Chongqing University, China, May 1, 2017 (10 pages).
Bao et al., https://github.com/baowenbo/DAIN, "DAIN (Depth-Aware Video Frame Interpolation)", IEEE Conference on Computer Vision and Pattern Recognition, Long Beach, CVPR 2019 (9 pages).
Dalca et al., "Unsupervised Learning of Probabilistic Diffeomorphic Registration for Images and Surfaces," Jul. 23, 2019 (18 pages).
Garyfallidis et al., "Dipy, a library for the analysis of diffusion MRI data," Frontiers in Neuroinformatics, vol. 8, art. 8, Feb. 21, 2014 (17 pages).
DIPY—Diffusion Imaging in Python; https://dipy.org/; accessed Mar. 1, 2021 (8 pages).
Daubechies, Ingrid, "Ten Lectures on Wavelets," CBMS-NSF Regional Conference Series in Applied Mathematics, Sep. 1992 (342 pages).
Farneback, Gunnar, "Very High Accuracy Velocity Estimation using Orientation Tensors, Parametric Motion, and Simultaneous Segmentation of the Motion Field," Proceedings Eighth IEEE International Conference on Computer Vision, Jul. 2001 (7 pages).
Felsberg and Sommer, "The monogenic signal," IEEE Transactions on Signal Processing, (49), 12, 3136-3144, 2001 (10 pages).
Chapter 2: Multiscale Vessel Enhancement Filtering, pp. 7-16, adapted from: Frangi et al., "Multiscale Vessel Enhancement Filtering," Medical Image Computing and Computer-Assisted Intervention—MICCAI'98, Lecture Notes in Computer Science, vol. 1496, Springer Verlag, Berlin, Germany, pp. 130-137, 1998 (10 pages).
Freeman and Adelson, "The Design and Use of Steerable Filters," IEEE Transactions on Pattern Analysis and Machine Intelligence, vol. 13, No. 9, pp. 891-906, Sep. 1991 (16 pages).
Gabor, D., "Theory of Communication," Sep. 24, 1945 (29 pages).
Goupillaud et al., "Cycle-Octave and Related Transforms in Seismic Signal Analysis," Geoexploration, 23, (1984/85), pp. 85-102 (18 pages).
Harris and Stephens, "A Combined Corner and Edge Detector," Alvey Vision Conference, pp. 147-151, 1988 (5 pages).
Horn and Schunck, "Determining Optical Flow," Artificial Intelligence 17, pp. 185-203, 1981 (19 pages).
Wolfram Research, "ImageDisplacements," Wolfram Language function, https://reference.wolfram.com/language/ref/ImageDisplacements.html, 2016 (5 pages).
Lucas and Kanade, "An Iterative Image Registration Technique with an Application to Stereo Vision," Proceedings DARPA Image Understanding Workshop, Apr. 1981, pp. 121-130 (10 pages).
Morlet et al., "Wave propogation and sampling theory—Part I: Complex signal and scattering in multilayered media," Geophysics, vol. 47, No. 2, Feb. 1982, pp. 203-221 (19 pages).
Shi and Tomasi, "Good Features to Track," IEEE Conference on Computer Vision and Pattern Recognition, Seattle, Jun. 1994 (8 pages).
Simoncelli and Farid, "Steerable Wedge Filters for Local Orientation Analysis," IEEE Transactions on Image Processing, 5(9): 1377-1382, 1996 (10 pages).
Unser and Van De Ville, "Wavelet Steerability and the Higher-Order Riesz Transform," IEEE Transactions on Image Processing, vol. 19, No. 3, Dec. 22, 2009 (17 pages).
Yin et al., "Reducing the X-ray radiation exposure frequency in cardio-angiography via deep-learning based video interpolation," Jun. 1, 2020 (6 pages).
Zhao et al., Ultrasound Contrast Imaging Based on a Novel Algorithm Combined Pulse Inversion with Wavelet Transform, Ultrasound in Medicine & Biology, 2011, vol. 37, No. 8, pp. 1292-1305.
Faubel et al., Cilia-based flow network in the brain ventricles, Neurophysiology, Jul. 8, 2016, vol. 353, iss. 6295, pp. 176-178.
Marshall et al., Cilia orientation and the fluid mechanics of development, Current Opinion in Cell Biology, 2008, vol. 20(1), pp. 48-52.
Ohata et al., Mechanosensory Genes Pkd1 and Pkd2 Contribute to the Planar Polarization of Brain Ventricular Epithelium, The Journal of Neuroscience, Aug. 5, 2015, vol. 35(31), pp. 11153-11168.
Jalalvand et al., Ciliated neurons lining the central canal sense both fluid movement and pH through ASIC3, Nature Communications, Jan. 8, 2016, pp. 1-12.
Wagshul et al., Resonant and notch behavior in intracranial pressure dynamics, J Neurosurgery Pediatrics, May 2009, vol. 3(5), pp. 354-364.
Park et al., Alterations of pulsation absorber characteristics in experimental hydrocephalus, J Neurosurg Pediatrics, Aug. 2010, vol. 6(2), pp. 159-170.
Kotelnikov, On the transmission capacity of the "ether" and of cables in electrical communication, Proceedings of the first All-Union Conference on the technological reconstruction of the communications sector and low-current engineering, Moscow 1933, vol. 1, pp. 1-23.
Sagel et al., Gated computed tomography of the human heart, Investigative radiology, Nov.-Dec. 1977, vol. 12, iss. 6, pp. 563-566.

(56) References Cited

OTHER PUBLICATIONS

Sarode et al., Video Motion Magnification Using Spatio-Temporal Algorithm, International Journal of Computer Applications (0975-8887), Jun. 2014, vol. 96, No. 9, pp. 9-13.
Zhao et al., Phase-Resolved Optical Coherence Tomography and Optical Doppler Tomography for Imaging Blood Flow in Human Skin with Fast Scanning Speed and High Velocity Sensitivity, Optics Letters, Jan. 15, 2000, vol. 25, iss. 2, pp. 114-116.
Yazdanfar et al., High Resolution Imaging of In vivo Cardiac Dynamics Using color Doppler Optical Coherence Tomography, Optics Express, Dec. 22, 1997, vol. 1, No. 13, pp. 424-431.
Wu et al., Eulerian Video Magnification for Revealing Subtle Changes in the World, ACM Transactions on Graphics, Jul. 1, 2012, vol. 31, iss. 4, pp. 1-8.
Wang et al., Phase-Sensitive Optical Coherence Elastography for Mapping Tissue Microstains in Real Time, Applied Physics Letter, 2007, vol. 90, pp. 164105-1-164105-3.
Robles et al., Assessing Hemoglobin Concentration Using Spectroscopic Optical Coherence Tomography for Feasibility of Tissue Diagnostics, Biomedical Optics Express, Aug. 2, 2010, vol. 1, No. 1, pp. 310-317.
Lahiri et al., Medical Applications of Infrared Thermography: A Review, Infrared Physics & Technology, 2012, vol. 55, pp. 221-235.
Mourant et al., Hemoglobin Parameters from Diffuse Reflectance Data, Journal of Biomedical Optics, Mar. 2014, vol. 19, iss. 3, pp. 037004-1-037004-9.
Makita et al., Optical Coherence Angiography, Optics Express, Aug. 21, 2006, vol. 14, No. 17, pp. 7821-7840.
Chen et al., Noninvasive Imaging of in vivo blood flow velocity using optical Doppler tomography, Optics Letters, Jul. 15, 1997, vol. 22, No. 14, pp. 1119-1121.
Izatt et al., In vivo bidirectional color Doppler flow imaging of picoliter blood volumes using optical coherence tomography, Optics Letters, Sep. 15, 1997, vol. 22, No. 18, pp. 1439-1441.
Drexler, Ultrahigh-Resolution Optical Coherence Tomography, Journal of Biomedical Optics, Jan./Feb. 2004, vol. 9, iss. 1, pp. 47-74.
Devor et al., Frontiers in optical imaging of cerebral blood flow and metabolism, Journal of Cerebral Blood Flow & Metabolism, 2012, vol. 32, pp. 1259-1276.
Chen et al., Optical Doppler Tomography, IEEE Journal on Selected Topics in Quantum Electronics, Jul. 1, 1999, vol. 5, No. 4, pp. 1134-1142.
Bachmann et al., Fluorescence Spectroscopy of Biological Tissues—A Review, Applied Spectroscopy Reviews, 2006, vol. 41, pp. 575-590.
Desmettre et al., Fluorescence Properties and Metabolic Features of Indocyanine Green (ICG) as Related to Angiography, Survey of Ophthalmology, Jul.-Aug. 2000, vol. 45, No. 1, pp. 15-27.
Martin et al., Hydrodynamic and longitudinal impedance analysis of cerebrospinal fluid dynamics at the craniovertebral junction in type I Chiari malformation, PloS One, Oct. 2013, vol. 8, iss. 10, pp. 1-9.
Abdallah, Considerations in perioperative assessment of valproic acid coagulopathy, review article, Journal of Anaesthesiology Clinical Pharmacology, Jan.-Mar. 2014, vol. 30, iss. 1, pp. 7-9.
D'Agnolo et al., Radon-Penrose transform for D-modules, Sep. 6, 1994, pp. 1-37.
Penkov, A Geometric Approach to the Linear Penrose Transform, Transactions of the American Mathematical Society, Aug. 1985, vol. 290, No. 2, pp. 555-575.
Wolfram, Statistical mechanics of cellular automata, The American Physical Society, Reviews of Modern Physics, vol. 55, No. 3, Jul. 1983, pp. 601-644.
Sturm et al., New Brain Tumor Entities Emerge from Molecular Classification of CNS-PNETs, Cell, Feb. 25, 2016, vol. 164, iss. 5, pp. 1060-1072.
Liebling et al., Wavelet-based Synchronization of Nongated Confocal Microscopy Data for 4D Imaging of the Embryonic Heart, Proceedings of SPIE 5914, Wavelets XI, 2005, vol. 591409, 6 pages.
Ehrenreich et al., New developments in the understanding of cerebral vasoregulation and vasospasm: the endothelin-nitric oxide network, CME Credit, Cleveland Clinic Journal of Medicine, Mar.-Apr. 1995, vol. 62, No. 2, pp. 105-116.
Vagharshakyan et al., Light Field Reconstruction Using Shearlet Transform, Sep. 29, 2015, pp. 1-12 (Cornell University Archive, https://arxiv.org/abs/1509.08969, arXiv:1509.08969v1).
Daubechies, Orthonormal Bases of Compactly Supported Wavelets, Communications on Pure and Applied Mathematics, 1988, vol. XLI, pp. 909-996.
Mandelshtam, The Multidimensional Filter Diagonalization Method, Journal of Magnetic Resonance, 2000, vol. 144, pp. 343-356.
Insolera et al., Cortical neurogenesis in the absence of centrioles, Nat Neurosci, Nov. 2014, vol. 17, No. 11, pp. 1528-1536.
Kool et al., Molecular subgroups of medulloblastoma: an international meta-analysis of transcriptome, genetic aberrations, and clinical data of WNT, SHH, Group 3, and Group 4 medulloblastomas, 2012, Acta Neuropathol, vol. 123, pp. 473-484.
Kutyniok et al., Compactly Supported Shearlets, Approximation Theory XIII: San Antonio 2010, pp. 1-24.
Liner, An overview of wavelet transform concepts and applications, University of Houston, Feb. 26, 2010, pp. 1-17.
Liu et al., Motion Magnification, ACM Transactions on Graphics (TOG), Jul. 2005, vol. 24, iss. 3, pp. 519-526 (8 pages).
Lohani et al., Intrasacral meningocele in the pediatric population, J Neurosurg Pediatrics, Jun. 2013, vol. 11, pp. 615-622.
Long et al., Spatiotemporal wavelet analysis for functional MRI, NeuroImage, 2004, vol. 23, pp. 500-516.
Maltz et al., Fixed gantry tomosynthesis system for radiation therapy image guidance based on a multiple source x-ray tube with carbon nanotube cathodes, Medical Physics, May 2009, vol. 36, No. 5, pp. 1624-1636.
Mandelshtam, FDM: the filter diagonalization method for data processing in NMR experiments, Progress in Nuclear Magnetic Resonance Spectroscopy, 2001, vol. 38, pp. 159-196.
Mourant et al., Hemoglobin parameters from diffuse reflectance data, Journal of Biomedical Optics, Mar. 2014, vol. 19, No. 3, pp. 037004-1-037004-9.
D'Ariano, How to Derive the Hilbert-Space Formulation of Quantum Mechanics From Purely Operational Axioms, 20 pages (presented at conference "On the Present Status of Quantum Mechanics" held on Sep. 7-9, 2005, Mali Losinj, Croatia) (Cornell University Archive, https://arxiv.org/abs/quant-ph/0603011, arXiv:quant-ph/0603011v1).
Mixter, Ventriculoscopy and Puncture of the Floor of the Third Ventricle, Boston M. & S. Journal, Mar. 1, 1923, vol. 188, No. 9, pp. 277-278.
Moussa et al., Efficacy of postoperative antibiotic injection in and around ventriculoperitoneal shunt in reduction of shunt infection: A randomized controlled trial, Clinical Neurology and Neurosurgery, 2016, vol. 143, pp. 144-149.
Monici, Cell and tissue autofluorescence research and diagnostic applications, Biotechnology Annual Review, 2005, vol. 11, pp. 227-256.
Drexler et al., In vivo ultrahigh-resolution optical coherence tomography, Optics Letters, Sep. 1, 1999, vol. 24, No. 17, pp. 1221-1223.
Rees et al., Role of endothelium-derived nitric oxide in the regulation of blood pressure, Proc. Natl. Acad. Sci. USA, 1989, vol. 86, pp. 3375-3378.
Rodino et al., The Gabor Wave Front Set (2013) (Cornell University Archive, https://arxiv.org/abs/1207.5628, arXiv:1207.5628v2), pp. 1-29.
Schaer et al., Haptoglobin Preserves Vascular Nitric Oxide Signaling during Hemolysis, American Journal of Respiratory and Critical Care Medicine, May 15, 2016, vol. 193, iss. 10, pp. 1111-1122.
Shumacher, Analog clock and watch reader, 2015, pp. 1-10 (https://www.cs.bgu.ac.il/~ben-shahar/Teaching/Computational-Vision/StudentProjects/ICBV151/ICBV-2015-1-ChemiShumacher/Report.pdf).
Tudor et al., Endoscopic third ventriculostomy (ETV) for idiopathic normal pressure hydrocephalus (iNPH) (Review), Cochran Collection, Cochrane Database of Systematic Reviews, 2015, iss. 7, pp. 1-23.

(56) References Cited

OTHER PUBLICATIONS

Khandelwal et al., Age-dependent increase in green autofluorescence of blood erythrocytes, J. Biosci. Sep. 2007, vol. 32, No. 6, pp. 1139-1145.
Wadhwa et al., Phase-Based Video Motion Processing, MIT Computer Science and Artificial Intelligence Lab, ACM Transactions on Graphics, Jul. 2013, vol. 32, No. 4, article 80, pp. 80:1-80:9.
Yang et al., Improved phase-resolved optical Doppler tomography using the Kasai velocity estimator and histogram segmentation, Optics Communications, Jul. 15, 2002, vol. 208, pp. 209-214.
Zhang et al., Orthogonal Complex Filter Banks and Wavelets: Some Properties and Design, IEEE Transactions on Signal Processing, Apr. 1999, vol. 47, No. 4, pp. 1039-1048.
Aaslid et al., Cerebral Autoregulation Dynamics in Humans, Stroke, 1989, vol. 20, pp. 45-52.
Adams et al., Symptomatic Occult Hydrocephalus with "Normal" Cerebrospinal-Fluid Pressure, A Treatable Syndrome, The New England Journal of Medicine, Jul. 15, 1965, vol. 273, No. 3, pp. 117-126.
Barina, Gabor Wavelets in Image Processing, Feb. 10, 2016, 6 pages (Cornell University Archive, https://arxiv.org/pdf/1602.03308.pdf, arXiv:1602.03308v1).
Bernardes et al., Digital Ocular Fundus Imaging: A Review, Ophthalmologica, 2011, vol. 226, pp. 161-181.
Bernardino et al., A Real-Time Gabor Primal Sketch for Visual Attention, Second Iberian Conference on Pattern Recognition and Image Analysis, 2005, 8 pages (http://vislab.isr.ist.utl.pt/publications/05-ibpria-alex.pdf).
Guo et al., Wavelets with composite dilations and their MRA properties, Applied and Computational Harmonic Analysis, 2006, vol. 20, pp. 202-236.
Goh et al., Subependymal giant cell tumors in tuberous sclerosis complex, Neurology, Oct. 2004, vol. 63, pp. 1457-1461.
Bo et al., Symbolic Representations in Motor Sequence Learning, Neuroimage, 2011, vol. 54, No. 1, pp. 417-426.
Bodranghien et al., Consensus Paper: Revisiting the Symptoms and Signs of Cerebellar Syndrome, Cerebellum, Jun. 2016, vol. 15, No. 3, pp. 369-391 (published online Jun. 2015) (23 pages).
Borsdorf et al., Separate CT-Reconstructions for 3D Wavelet Based Noise Reduction Using Correlation Analysis, 2007, IEEE Nuclear Science Symposium Conference Record, pp. 2633-2638.
Brouder et al., A Smooth Introduction to the Wavefront Set, Apr. 7, 2014, pp. 1-29 (Cornell University Archive, https://arxiv.org/pdf/1404.1778.pdf, arXiv:1404.1778v1).
Burt et al., The Laplacian Pyramid as a Compact Image Code, IEEE Transactions on Communications, Apr. 1983, vol. COM-31, No. 4, pp. 532-540.
Candes et al., New Tight Frames of Curvelets and Optimal Representations of Objects with C2 Singularities, Nov. 2002, pp. 1-39 (http://citeseerx.ist.psu.edu/viewdoc/download?doi=10.1.1.162.1548&rep=rep1&type=pdf).
Cense et al., Ultrahigh-resolution high-speed retinal imaging using spectral-domain optical coherence tomography, Optics Express, May 31, 2004, vol. 12, No. 11, pp. 2435-2447 (13 pages).
Cheng et al., Mammalian DNA Methyltransferases: A Structural Perspective, Structure, Review, Mar. 2008, vol. 16, No. 3, pp. 341-350.
Coumans et al., Volumetric analysis of syringomyelia following hindbrain decompression for Chiari malformation Type I : syringomyelia resolution follows exponential kinetics, Neurosurg Focus, Sep. 2011, vol. 31, No. 3:E4, pp. 1-4.
Dahmen, Wavelet and Multiscale Methods for Operator Equations, 1997 (146 pages).
Deutsch et al., Information Flow in Entangled Quantum Systems, (1999) pp. 1-24 (https://arxiv.org/ftp/quant-ph/papers/9906/9906007.pdf).
Donoho, Compressed Sensing, Sep. 14, 2004, pp. 1-34.
Donoho et al., Message-Passing Algorithms for Compressed Sensing, PNAS, Nov. 10, 2009, vol. 106, No. 45, pp. 18914-18919.
Duverger et al., Concentrations of Putative Neurovascular Transmitters in Major Cerebral Arteries and Small Pial Vessels of Various Species, Journal of Cerebral Blood Flow and Metabolism, 1987, vol. 7, No. 4, pp. 497-501.
Eastwood, The Penrose Transform for Complex Projective Space, Cornell University Archive, Aug. 17, 2008, pp. 1-11 (https://arxiv.org/abs/0808.2321, arXiv:0808.2321v1).
Eastwood et al., Cohomology and Massless Fields, Commun. Math. Phys. (1981) vol. 78, pp. 305-351.
Edelman et al., Nitric Oxide: Linking Space and Time in the Brain, Proc. Natl. Acad. Sci. USA, Dec. 1992, vol. 89, pp. 11651-11652.
Feichtinger et al., Gabor Frames and Time-Frequency Analysis of Distributions, Journal of Functional Analysis, 1997, vol. 146, No. FU963078, pp. 464-495.
Feng et al., Conservation and Divergence of Methylation Patterning in Plants and Animals, PNAS, May 11, 2010, vol. 107, No. 19, pp. 8689-8694.
Fisher et al., Group Formation, Relatedness, and the Evolution of Multicellularity, Current Biology, Jun. 17, 2013, vol. 23, No. 12, pp. 1120-1125.
Fujimoto et al., Optical Coherence Tomography: An Emerging Technology for Biomedical Imaging and Optical Biopsy, Neoplasia, Jan.-Apr. 2000, vol. 2, Nos. 1-2, pp. 9-25.
Goriely et al., Mechanics of the brain: perspectives, challenges, and opportunities, Biomech Model Mechanobiol, 2015, vol. 14, pp. 931-965.
Guerquin-Kern et al., A Fast Wavelet-Based Reconstruction Method for Magnetic Resonance Imaging, IEEE Transactions on Medical Imaging, Institute of Electrical and Electronics Engineers, 2011, 14 pages (obtained from HAL archives-ouvertes).
Guo et al., Sparse Multidimensional Representations using Anisotropic Dilation and Shear Operators, 2005, 13 pages (https://www.math.uh.edu/~dlabate/Athens.pdf).
Han, Properties of Discrete Framelet Transforms, Math. Model. Nat. Phenom., 2013, vol. 8, No. 1, pp. 18-47 (32 pages).
Heil, What is a Frame?, Notices of the AMS, 2013, vol. 60, No. 6, pp. 748-750.
Herz et al., Ultrahigh resolution optical biopsy with endoscopic optical coherence tomography, Optics Express, Jul. 26, 2004, vol. 12, No. 15, pp. 3532-3542.
Hogeweg, Cellular Automata as a Paradigm for Ecological Modeling, Applied Mathematics and Computation, 1988, vol. 27, pp. 81-100.
Hormander, The Spectral Function of an Elliptic Operator, Acta Math, May 7, 1968, vol. 121, pp. 193-218.
Huff et al., Dnmt1-Independent CG Methylation Contributes to Nucleosome Positioning in Diverse Eukaryotes, Cell, Mar. 13, 2014, vol. 156, No. 6, pp. 1286-1297.
Januszewski et al., Flow-based evaluation of cerebral revascularization using near-infrared indocyanine green videoangiography, Neurosurg Focus, Feb. 2014, vol. 36, No. 2: E14, pp. 1-8.
Jia et al., Quantitative OCT angiography of optic nerve head blood flow, Biomedical Optics Express, Dec. 1, 2012, vol. 3, No. 12, pp. 3127-3137.
Kamble et al., A Review: Eulerian Video Motion Magnification, International Journal of Innovative Research in Computer and Communication Engineering, Mar. 2015, vol. 3, iss. 3, pp. 2384-2390.
Kim et al., Epigenetic mechanisms in mammals, Cellular and Molecular Life Sciences, 2009, vol. 66, pp. 596-612.
Kittipoom et al., Construction of Compactly Supported Shearlet Frames, Cornell University Archive, 2010, pp. 1-37 (https://arxiv.org/abs/1003.5481, arXiv:1003.5481v2).
Klimenko et al., A cross-correlation technique in wavelet domain for detection of stochastic gravitational waves, 2002, pp. 1-15 (https://arxiv.org/abs/gr-qc/0208007, arXiv:gr-qc/0208007v1).
Knopfmacher et al., Graphs, partitions and Fibonacci numbers, Discrete Applied Mathematics, 2007, vol. 155, pp. 1175-1187.
Koenig et al., Regression of Subependymal Giant Cell Astrocytoma With Rapamycin in Tuberous Sclerosis Complex, J Child Neurol., Oct. 2008, vol. 23, No. 10, pp. 1238-1239.
Kramer et al., Intraventricular fibrinolysis with tissue plasminogen activator is associated with transient cerebrospinal fluid inflamma-

(56) References Cited

OTHER PUBLICATIONS tion: a randomized controlled trial, Journal of Cerebral Blood Flow & Metabolism, 2015, vol. 35, pp. 1241-1248.
Kutyniok et al., Resolution of the Wavefront Set using Continuous Shearlets, Transactions of the American Mathematical Society, May 2009, vol. 361, No. 5, pp. 2719-2754.
Kutyniok et al., Image Separation using Wavelets and Shearlets, International Conference on Curves and Surfaces, 2010, pp. 1-14 (https://www.math.tu-berlin.de/fileadmin/i26_fg-kutyniok/Kutyniok/Papers/ImageSeparation.pdf).
Lee, Wavelet-Vaguelette Decompositions and Homogeneous Equations, Dec. 1997, Purdue University, In Partial Fulfillment of the Requirements for the Degree of Doctor of Philosophy, 103 pages.
Lindenmayer, Developmental Algorithms for Multicellular Organisms: A Survey of L-Systems, J. Theor. Biol., 1975, vol. 54, pp. 3-22.
Lopez et al., The Cauchy problem for a forced harmonic oscillator, Revista Mexicana De Fisica, Dec. 2009, vol. 55, No. 2, pp. 196-215.
Luney et al., Acute Posterior Cranial Fossa Hemorrhage—Is Surgical Decompression Better than Expectant Medical Management?, Neurocritical Care, Apr. 12, 2016, 6 pages.
Gabor, Theory of Communication, Part 3: Frequency Compression and Expansion, 1946, vol. 93, No. 26, pp. 445-457.
Havla et al., Wavelet-based calculation of cerebral angiographic data from time-resolved CT perfusion acquisitions, Eur Radiol. Aug. 2015, vol. 25, No. 8, pp. 2354-2361 (published online Feb. 26, 2015) (8 pages).
Kamp et al., Microscope-Integrated Quantitative Analysis of Intraoperative Indocyanine Green Fluorescence Angiography for Blood Flow Assessment: First Experience in 30 Patients, Operative Neurosurgery 1, vol. 70, Mar. 2012, pp. ons65-ons74.
Mazzola et al., Pediatric Hydrocephalus: systematic literature review and evidence-based guidelines. Part 2: Management of posthemorrhagic hydrocephalus in premature infants, Nov. 2014, J Neurosurg Pediatrics (Suppl), vol. 14, pp. 8-23.
Mccrory et al., Consensus statement on concussion in sport: the 4th International Conference on Concussion in Sport held in Zürich, Nov. 2012, Br J Sports Med, (2013), vol. 47, pp. 250-258.
Michod et al., Cooperation and Conflict in the Evolution of Multicellularity, 2001, The Genetics Society of Great Britain, Heredity, vol. 86, pp. 1-7.
Nehra et al., Peyronie's Disease: AUA Guideline, American Urological Association (AUA) Guideline, approved Apr. 2015, pp. 1-41.
Forbes et al., Statistical Distributions, Fourth Edition, copyright 2011, John Wiley and Sons, Inc., Chapters 1-9, (84 pages).
Mandelshtam et al., Harmonic inversion of time signals and its applications, AIP The Journal of Chemical Physics 1997, vol. 107, No. 6756, 12 pages.
Schroeder, The Simple Harmonic Oscillator, copyright 2015-2016, 5 pages (https://physics.weber.edu/schroeder/quantum/Harmonic.pdf).
International Standards Organization, ISO/IEC 14496-12 Multimedia Formats Information Technology—Coding of audio-visual objects (2008) 4 pages (Abstract).
Guido et al., Introduction to the special issue on wavelet-based algorithms for medical problems (2007) vol. 37, p. 429.
Zhang et al., "Application of Wavelet Thresholding De-noising in DSA," International Symposium on Information Science and Engineering IEEE Computer Society, 2008, pp. 130-134.
Akram et al., "Blood Vessel Enhancement and Segmentation Using Wavelet Transform, International Conference on Digital Image Processing IEEE Computer Society," 2009, pp. 34-38.
Cao et al., "Joint Spatio-Temporal Registration and Microvasculature Segmentation of Retinal Angiogram Sequences," 33rd Annual International Conference of the IEEE EMBS, 2011, pp. 2618-2621.
Tsai et al., "Motion Estimation and Wavelet Transform in Angiogram Video Coding," IEEE, 1994, pp. 1121-1125.

Oh et al., "Reversible Wavelet Compression for Digital Angiograms," Proceedings of the 20th Annual International Conference of the IEEE Engineering in Medicine and Biology Society,1998, vol. 20, No. 3, pp. 1442-1445.
Tache et al., "Enhanced Visualization of Cerebral Blood Vessels for X-ray Angiograms," IEEE International Conference on E-Health and Bioengineering, 2013, pp. 1-13.
Sun et al., "Morphological enhancement of vascular angiogram with multiscale detected by Gabor filters," Electronics Letters, 2008, vol. 44, No. 2, pp. 1-3.
Munteanu et al., "Wavelet-Based Lossless Compression of Coronary Angiographic Images," IEEE Transactions on Medical Imaging, 1999, vol. 18, No. 3, pp. 272-281.
Lin et al., "Extraction of Coronary Arterial Tree Using Cine X-Ray Angiograms," Biomedical Engineering—Applications, Basis & Communications, 2005, pp. 111-120.
Hohne et al., "Fourier Domain Techniques for Digital Angiography of the Heart," IEEE Transactions on Medical Imaging, 1984, vol. MI-3, No. 2, pp. 62-67.
Hohne et al., "Proceedings of SPIE: Digital Angiography of the Heart in the Frequency Domain," Medical Images and Icons IEEE, 1984, pp. 245-250.
Havla et al., "Validation of a method to differentiate arterial and venous vessels in CT perfusion data using linear combinations of quantitative time-density curve characteristics," Eur. Radiol., 2015, vol. 25, pp. 2937-2944.
Farge, M., "Wavelet Transforms and Their Applications to Turbulence," Annu. Rev. Fluid Mech., 1992, vol. 24, pp. 395-457.
Havla, et al., "Classification of arterial and venous cerebral vasculature based on wavelet postprocessing of CT perfusion data," Med. Phys. (2016) 43 (2), pp. 702-709.
Nielsen, Conditions for a Class of Entanglement Transformations, Aug. 17, 1999, pp. 1-4 (Cornell University Archive, arXiv No. quant-ph/9811053v2).
Novotny et al., A Method of Photographing Fluorescence in Circulating Blood in the Human Retina, Circulation, vol. XXIV, Jul. 1961, pp. 82-86.
Pewsey et al., Circular Statistics in R, Oxford University Press, (2013) Chapters 1-3, 7 and Appendix (80 pages).
Pfister et al., Molecular diagnostics of CNS embryonal tumors, Acta Neuropathology, Nov. 2010, vol. 120, No. 5, pp. 553-566.
Pollock, Dyadic Wavelets Analysis, (2016) pp. 1-26.
Qian et al., High Resolution Stationary Digital Breast Tomosynthesis using Distributed Carbon Nanotube X-ray Source Array, Medical Physics, (Apr. 2012) vol. 39, No. 4, pp. 2090-2099.
Rashid-Farrokhi et al., Wavelet-Based Multiresolution Local Tomography, IEEE Transactions on Image Processing, Oct. 1997, vol. 6, No. 10, pp. 1412-1430.
Rollins et al., Real-time in vivo color Doppler optical coherence tomography, Journal of Biomedical Optics, Jan. 2002, vol. 7, No. 1, pp. 123-129.
Ronneberger et al., U-Net: Convolutional Networks for Biomedical Image Segmentation, May 18, 2015, pp. 1-8 (Cornell University Archive, arXiv No. 1505.04597v1).
Ruzhansky, Introduction to pseudo-differential operators, Jan. 21, 2014, pp. 1-54.
Sadowsky, The Continuous Wavelet Transform: A Tool for Signal Investigation and Understanding, John Hopkins APL Technical Digest, 1994, vol. 15, No. 4, pp. 306-318.
Saito et al., Efficient Gene Transfer into the Embryonic Mouse Brain Using in Vivo Electroporation, Developmental Biology, 2001, vol. 240, pp. 237-246.
Sen et al., 3D ROI Image Reconstruction from Truncated Computed Tomogrpahy, IEEE Transactions on Medical Imaging, May 26, 2013, pp. 1-24.
Shen et al., Growth hormone therapy and risk of recurrence/progression in intracranial tumors: a meta-analysis, Neurol Sci, 2015, vol. 36, pp. 1859-1867.
Shy et al., X-Y separable pyramid steerable scalable kernels, (1994) pp. 237-244 (https://authors.library.caltech.edu/3438/1/SHYcvpr94.pdf).
Valens, A Really Friendly Guide to Wavelets, 1999, pp. 1-19.

(56) References Cited

OTHER PUBLICATIONS

Vrhel et al., Fast Computation of the Continuous Wavelet Transform through Oblique Projections, (1996) pp. 1-4 (http://citeseerx.ist.psu.edu/viewdoc/download?doi=10.1.1.66.3780&rep=rep1&type=pdf).
Wang et al., Three dimensional optical angiography, Optics Express, Apr. 2, 2007, vol. 15, No. 7, pp. 4083-4097.
Wang et al., Doppler optical micro-angiography for volumetric imaging of vascular perfusion in vivo, May 25, 2009, Optics Express, vol. 17, No. 11, pp. 8926-8940.
Wunsch, Microlocal Analysis and Evolution Equations: Lecture Notes from 2008 CMI/ETH Summer School, 2012 (92 pages).
Yang et al., The X-Ray Transform Projection of 3D Mother Wavelet Function, Research Article, Computational and Mathematical Methods in Medicine, 2013, Article ID 754829, 9 pages.
Zhu et al., Endothelial nitric oxide synthase: a potential therapeutic target for cerebrovascular diseases, Molecular Brain, 2016, vol. 9, No. 30, pp. 1-8.
Zhuang et al., Fan-beam and cone-beam image reconstruction via filtering the backprojection image of differentiated projection data, Institute of Physics Publishing, Physics in Medicine and Biology, 2004, vol. 49, pp. 5489-5503.
Taylor et al., Molecular subgroups of medulloblastoma: the current consensus, Consensus Paper, Acta Neuropathol, 2012, vol. 123, pp. 465-472.
Thavavel et al., Regularized Computed Tomography using Complex Wavelets, International Journal of Magnetic Resonance Imaging, 2007, vol. 01, No. 01, pp. 027-032.
Thielen et al., Ultrafast dynamic computed tomography myelography for the precise identification of high-flow cerebrospinal fluid leaks caused by spiculated spinal osteophytes, J Neurosurg Spine, Clinical Article, Mar. 2015, vol. 22, pp. 324-331.
Spaide et al., Retinal Vascular Layers Imaged by Fluorescein Angiography and Optical Coherence Tomography Angiography, Original investigation, JAMA Opthalmology, Jan. 2015, vol. 133, No. 1, pp. 45-50.
Ren et al., Phase-resolved functional optical coherence tomography: simultaneous imaging of in situ tissue structure, blood flow velocity, standard deviation, birefirngence, and Stokes vectors in human skin, Optics Letters, Oct. 1, 2002, vol. 27, No. 19, pp. 1702-1704.
Shenoi, Introduction to Digital Signal Processing and Filter Design, Wiley, 2006, Chapters 3-5 (217 pages).
Srinivasan et al., Quantitative Cerebral Blood Flow with Optical Coherence Tomography, Optics Express, Feb. 1, 2010, vol. 18, No. 3, pp. 2477-2494.
Steane, An introduction to spinors, Dec. 13, 2013, pp. 1-23 (Cornell University Archive, arXiv No. 1312.3824v1).
Thompson et al., Prognostic Value of Medulloblastoma Extent of Resection After Accounting for Molecular Subgroup: A Retrospective Integrated Clinical and Molecular Analysis, Lancet Oncol. Apr. 2016, vol. 17, No. 4, pp. 484-495.
Timmons, Image-Guided Neurosurgery: Integration of Medical Image Data with a Real-time View of the Surgical Field, Jun. 1997, pp. 1-66.
Tran et al., Learning Spatiotemporal Features with 3D Convolutional Networks, Proceedings of the 2015 IEEE International Conference on Computer Vision (ICCV), (2015) pp. 4489-4497.
Rao et al., Shear strain imaging using shear deformations (2008) Med. Phys. 35(2):412-423.
Weaver et al., Brain mechanical property measurement using MRE with intrinsic activation Phys. Med. Biol. (2012) 57:7275-7287.
Kashif et al., Model-Based Noninvasive Estimation of Intracranial Pressure from Cerebral Blood Flow Velocity and Arterial Pressure, Sci. Transl. Med. (2012) vol. 4, No. 129, pp. 1-10.
Bayer et al., Two-Dimensional Simulations of Displacement Accumulation Incorporating Shear Stain, Ultrason. Imaging (2014) vol. 36(1):55-73.

Feingold et al., Quantitative volumetric perfusion mapping of the microvasculature using contrast ultrasound, Invest Radiol. (2010) 45:669-674.
Johnson et al., Local mechanical properties of white matter structures in the human brain, NeuroImage (2013) 79:145-152.
Khullar et al., Wavelet-based fMRI analysis: 3-D denoising, signal seperation, and validation metrics, NeuroImage (2011) 54:2867-2884.
Lee et al., Wavelet Methods for Inverting the Radon Transform with Noisy Data, IEEE Transactions on Image Processing, (2001) vol. 10, No. 1, pp. 79-94 (16 pages) (https://www.math.purdue.edu/~lucier/692/tomography.pdf).
Kutyniok et al., ShearLab 3D: Faithful Digital Shearlet Transforms based on Compactly Supported Shearlets, (2014) (39 pages) (Cornell University Archive, arXiv No. 1402.5670v1).
R-Forge User's Manual, (2011), SVN Revision: 227, 10 pages.
Daubechies Ten Lectures of Wavelets, Springer-Verlag, (1992), from CBMS-NSF Regional Conference Series in Applied Mathematics Society for Industrial and Applied Mathematics 1990 (344 pages).
Lawton, Seven Aneurysms Tenets and Techniques for Clipping (2011) Section 1, Thieme Medical Publishers, New York, Section 1, (36 pages).
Wendy Bottinor, MD, et al. "Adverse Reactions to Iodinated Contrast Media", International Journal of Angiology, vol. 22, No. Mar. 2013, Aug. 16, 2013, 5 pages.
Yumi Yanaga, et al., "Contrast Material Injection Protocol With the Dose Adjusted to the Body Surface Area for MDCT Aortography", AJR:194, Apr. 2010, 6 pages.
Keika Ose, et al., "'Gadolinium' as an Alternative to Iodinated Contrast Media for X-Ray Angiography in Patients With Severe Allergy", Circ J 2005; 69: 507-509, Circulation Journal, vol. 69, Apr. 2005, 3 pages.
H. Kälsch, M.D., et al., "Gadolinium-Based Coronary Angiography in Patients with Contraindication for Iodinated X-Ray Contrast Medium: A Word of Caution", Journal of Interventional Cardiology, vol. 21, No. 2, 2008, 9 pages.
Rohit S. Loomba, MD, et al., "Comparison of Contrast Volume Radiation Dose, Fluoroscopy Time, and Procedure Time in Previously Published Studies of Rotational Versus Conventional Coronary Angiography", The American Journal of Cardiology, Am J Cardiol 2015; 116:43e49, 7 pages.
Hrvoje Lusic, et al., "X-Ray Computed Tomography Contrast Agents", Chem Rev. Mar. 13, 2013; 113(3), NIH-PA Author Manuscript, 64 pages.
Kreton Mavromatis, MD, "The Imperative of Reducing Contrast Dose in Percutaneous Coronary Intervention", Editorial Comment, JACC: Cardiovascular Interventions, vol. 7, No. 11, 2014, 3 pages.
Sun Y. Lee, et al., "A Review: Radiographic Iodinated Contrast Media-Induced Thyroid Dysfunction", J Clin Endocrinol Metab., Feb. 2015; 100(2): 376-383, Published online Nov. 6, 2014, 15 pages.
Romain Lacroix, "3D Optical flow analysis of a pulsed contrast agent in the bloodstream. Application to virtual angiography and Magnetic Particle Imaging", Medical Imaging, Télécom Bretagne; Université de Bretagne Occidentale, Apr. 5, 2016, English, tel-01298049, https://hal.archives-ouvertes.fr/tel-01298049/document, 48 pages.
Jerome Revaud, et al., "EpicFlow: Edge-Preserving Interpolation of Correspondences for Optical Flow", May 19, 2015, https://arxiv.org/pdf/1501.02565v2.pdf, 11 pages.
Navid Nourani-Vatani, et al., "A Study of Feature Extraction Algorithms for Optical Flow Tracking", Dec. 5, 2012, https://www.araa.asn.au/acra/acra2012/papers/pap105.pdf, 7 pages.

\* cited by examiner

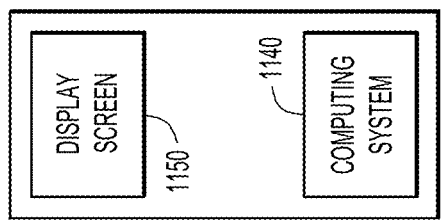
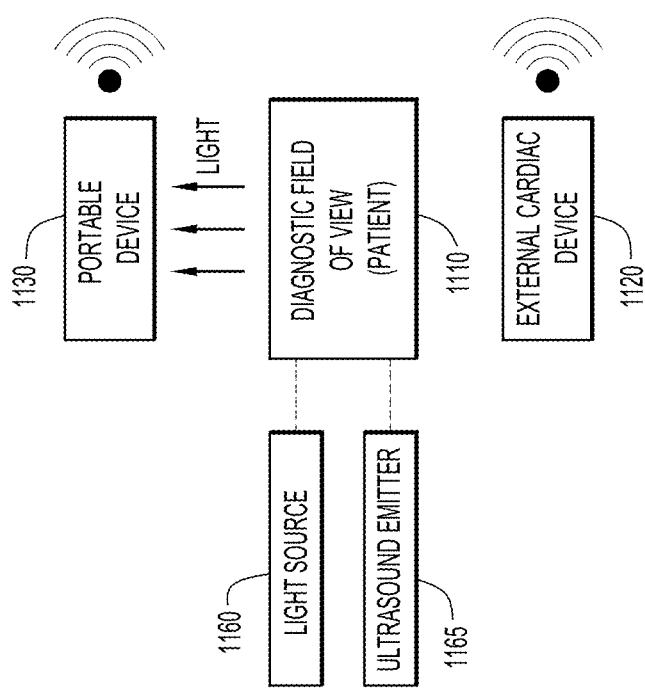
FIG.1B

INTRINSIC CONTRAST OPTICAL CROSS-CORRELATED WAVELET ANGIOGRAPHY

CROSS-REFERENCE TO RELATED APPLICATIONS

This application claims priority to U.S. Provisional Application No. 62/829,290 filed Apr. 4, 2019, the contents of which are hereby incorporated by reference in their entirety.

FIELD

The field generally relates to reconstruction of spatiotemporal images of a moving vascular pulse wave using wavelet mathematics or similar mathematical techniques applied to a sequence of angiographic images acquired at faster than cardiac rate, and in particular, to reconstruction of spatiotemporal images using intrinsic contrast.

BACKGROUND

An angiogram is an x-ray study in which a chemical contrast agent is injected into the bloodstream and a sequence of x-rays is obtained. The injected chemical contrast agent travels as a bolus through the vascular system and passes from the arterial subsystem through the capillaries to the venous subsystem. The chemical contrast agent blocks the passage of x-rays, allowing the geometry of the passing x-rays to produce an image upon arrival to a two-dimensional array of x-ray detectors. An example of an optical chemical contrast agent that is administered intravenously is indocyanine green (ICG). The chemical contrast agent is contained within the walls of blood vessels, and therefore, its spatial distribution corresponds with the intraluminal configuration of blood vessels. Blood in the systematic circulation flows unidirectionally in series from the heart to the arteries, through the capillaries, to the veins, and back to the heart. Accordingly, the angiogram may be used to distinguish properties of the arterial versus venous subsystems. Therefore, the relative timing of images within the angiographic image sequence conveys information about the vascular anatomy and physiology of particular circulatory subsystems. Angiographic images based on injected chemical contrast agent typically show spatial resolution of vascular structures (such as blood vessels) from non-vascular tissues, since the vessel wall forms a sharp boundary for the chemical contrast agent. Spatial resolution may be increased by increasing the injected dose of the chemical contrast agent. However, increasing the dosage often has morbid side effects, such as an increased risk of kidney damage, or for those patients with compromised kidney function, toxic side-effects. Thus, intravenously administered chemical contrast agents have a number of drawbacks, including toxicity, and are often not suitable for individuals with renal disease or other disorders.

Reconstruction of cine images of moving vascular pulse waves using cross-correlated wavelet mathematics applied to angiographic images acquired at faster than cardiac rate is taught by U.S. Pat. No. 10,123,761, which is incorporated by reference herein in its entirety. However, this approach captures data about cardiac frequency variation and motion based on intravenously injected contrast containing structures.

Other imaging techniques are known in the art. For example, Eulerian magnification, as taught by Wu in U.S. Pat. Nos. 9,811,901, 9,324,005 have been applied to produce amplified visual effects. These techniques rely on mathematical operations based on a Taylor expansion containing an amplification term. The procedure taught by Wu calls for the selection by the user of a spatial frequency cut off filter and an amplification factor $\alpha$. However, these techniques are distinct from the techniques provided in this application and do not provide a method for reconstructing cardiac frequency phenomena in angiographic data using intrinsic contrast.

Other imaging techniques, such as optical coherence tomography, have been used to generate three-dimensional images of the structure of a limited range of tissue including vascularized tissue. This technique may be employed with intravascularly injected chemical contrast such as fluorescein to generate optical angiograms in three-dimensions. The travel of erythrocytes generates a Doppler effect on the wavelengths of light employed in optical coherence tomography as taught by Chen (U.S. Pat. Nos. 6,549,801 and 7,359,062) and others.

While a variety of imaging techniques are available, imaging techniques capable of reconstructing cardiac frequency phenomena in angiographic data without intravenously administered contrast agents and/or with improved patient safety profiles are needed.

SUMMARY OF THE INVENTION

Embodiments of the invention are directed to methods, systems, and computer readable media for reconstructing cardiac frequency phenomena in angiographic data using intrinsic contrast. A time sequenced series of optical images of a patient is obtained by an optical system at a rate faster than cardiac frequency, wherein the time sequenced series of images capture one or more physical properties of intrinsic contrast. A cross-correland signal from the patient is obtained. A cross-correlated wavelet transform analysis is applied to the time sequenced series of optical images to yield a spatiotemporal representation of cardiac frequency phenomena. The cross-correlated wavelet transform analysis may comprise performing a wavelet transform on the time sequenced series of optical images to obtain a wavelet transformed signal, cross-correlating the wavelet transformed signal with the cross-correland signal to obtain a cross-correlated signal, filtering the cross-correlated signal at cardiac frequency to obtain a filtered signal, and performing an inverse wavelet transform on the filtered signal to obtain a spatiotemporal representation of the time sequences series of optical images. Images of the cardiac frequency phenomena may be generated from the spatiotemporal representation.

In an aspect, the spatiotemporal reconstruction is displayed in one or more reconstructed images.

In another aspect, a contemporaneously measured cardiac signal is obtained and cross-correlated with the wavelet transformed signal.

In an aspect, the images are obtained by optical microscopy, near-infrared microscopy, ultrasound, or Doppler technology.

In another aspect, images are obtained from imaging a body with a vascular structure.

In an aspect, intrinsic contrast comprises thermal radiation, optical reflection, or auto-fluorescence.

In another aspect, the reconstructed angiographic images are provided as a cine video sequence.

In an aspect, a second time sequenced series of images is acquired with intravenously injected chemical contrast and a second spatiotemporal representation of the images obtained from the intravenously injected chemical contrast is generated. The spatiotemporal representation of the images obtained with intrinsic contrast is paired with the second spatiotemporal representation of the images obtained from the intravenously injected chemical contrast. The second spatiotemporal representation of the images obtained with intrinsic contrast is calibrated based on the pairing.

Still other objects and advantages of these techniques will be apparent from the specification and drawings.

BRIEF DESCRIPTION OF THE DRAWINGS

Example embodiments of the invention are described with reference to the drawing figures, in which:

FIGS. 1A and 1B are schematic diagrams of example systems for utilizing intrinsic contrast optical angiography, according to aspects of the disclosure. FIG. 1A illustrates a system in which visible and near infrared signals are obtained in an operating room setting. FIG. 1B illustrates a mobile system.

DETAILED DESCRIPTION

Figure 1A:
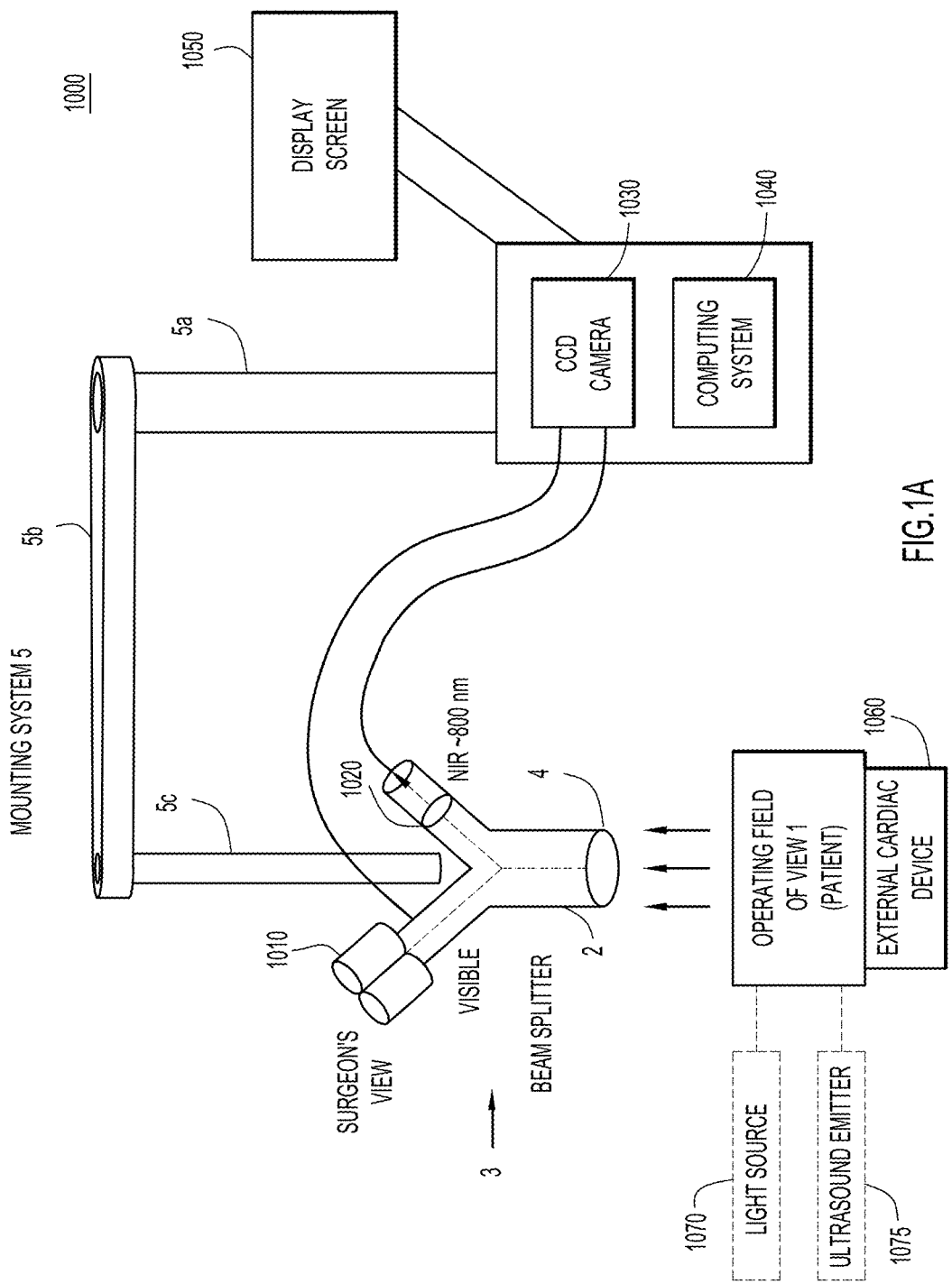

Present techniques are directed towards spatiotemporal reconstruction of cardiac frequency phenomena using intrinsic contrast and cross-correlated wavelet angiography. As used herein, the term "cross-correlated wavelet angiography" refers to reconstruction of spatiotemporal images of a moving vascular pulse wave by wavelet mathematics applied to a sequence of angiographic images acquired at faster than cardiac rate, e.g., as described in U.S. Pat. No. 10,123,761, which is incorporated by reference herein in its entirety.

In other aspects, other mathematical techniques may be used for reconstruction of spatiotemporal images of a moving vascular pulse wave with intrinsic contrast. For example, intrinsic contrast may be performed with other mathematical computational techniques, including windowed Fourier transforms. In still other examples, intrinsic contrast may be used with other techniques involving bandpass filters and amplifications, e.g., as provided in co-pending patent application Ser. No. 16/832,695, filed on Mar. 27, 2020, which is incorporated by reference herein in its entirety.

Present techniques allow spatiotemporal reconstruction to be performed using intrinsic contrast instead of an intravascularly administered contrast agent. This approach provides improved safety profiles and is suitable for patients with renal disorders. Optionally, present techniques may be used to perform both intrinsic contrast cross-correlated wavelet angiography and intravascularly administered contrast agent cross-correlated wavelet angiography. Still another option is to use the present techniques to perform intrinsic contrast cross-correlated wavelet angiography in combination with conventional angiography.

The term "intrinsic contrast," as used herein, refers to properties of the circulatory system that may be recorded without the administration of a chemical contrast agent and are localized to the circulatory system. Such properties have measureable distributions that may be used to form spatiotemporal reconstructed images. Examples of physical properties include variations in thermal radiation (detectable in the infrared and near infrared spectral electromagnetic ranges), variations in optical reflection in the visible electromagnetic spectrum (such as at a wavelength of 640 nm, where the optical differences between oxy-hemoglobin and deoxy-hemoglobin are maximized), variations in thermal emission (see, e.g., U.S. Pat. Nos. 5,637,871 and 3,335,716), and variations in auto-fluorescence (where illumination in the near infrared spectrum causes porphyrins and other molecules in blood to fluoresce in the near infrared spectrum), variations in optical tissue motion, or variations in any other physiological property that reflects vascular anatomy and physiology and may be imaged.

Given that the heart sends blood to the body as a sequence of arterial stroke volumes, intrinsic contrast (similar to intravenously injected contrast) varies at cardiac frequency. Furthermore, this variation is likely to be of greater magnitude within blood vessels, since vessels are connected by a continuous fluid column to the heart. Hence, the presence of cardiac frequency variation within the spatial distribution of intrinsic contrast may be a source of added spatial resolution insofar as cardiac frequency occurs inside or in proximity to blood vessels because blood is a continuous fluid column that connects to the ventricle of the heart. In some aspects, the cardiac frequency may fall within a range of 20-200 beats per minute in a human patient.

The beating of the heart produces cardiac frequency variation in intrinsic contrast and increases the signal to noise ratio in the imaging of intrinsic contrast, in turn offering a strategy for improved intrinsic contrast spatial resolution in the derived images. Furthermore, the arterial and venous circulatory subsystems may house vascular pulse waves that exhibit arteriovenous phase locking at cardiac frequency. This offers a strategy for resolving arterial from venous circulatory subsystems.

Accordingly, internal properties of a body, or properties having internal contrast, reflect vascular anatomy and physiology changes that may be captured via imaging. Present techniques apply cross-correlated wavelet angiography to cine optical data using intrinsic contrast. At steady physiological state, intrinsic contrast does not vary between one cardiac cycle and the next, and does not offer a bolus travel timing mechanism to distinguish the arterial from venous circulatory subsystems (although this distinction may be obtained from the relative oxy-hemoglobin and deoxy-hemoglobin signals at 640 nm). Even though intrinsic contrast does not offer a bolus travel mechanism to separate the venous from the arterial circulatory subsystems, the arterial and venous pathways pulse out of phase with each other, and this phase difference may serve as a criterion allowing intrinsic contrast angiography to separate the arterial from the venous circulatory systems in intrinsic contrast optical angiograms. Thus, instead of relying on bolus travel timing, the identification of selected anatomic and/or physical structures combined with filtering for structures pulsing in phase and/or in complementary phase may allow arterial and venous subsystems to be distinguished.

With intrinsic contrast, the signal difference in the foreground within vessels versus the background is less, thereby producing reduced spatial resolution of intrinsic contrast versus injected chemical contrast agent angiograms. Thus, angiographic images exploiting intrinsic contrast may have less temporal and less spatial resolution than those images obtained from an injected chemical contrast agent. However, with intrinsic contrast, there is no associated toxicity from administration of chemical contrast. Present techniques provide for spatiotemporal reconstruction of vascular pulse waves from cine images of these intrinsic contrast phenomena acquired at faster than cardiac rate by cross-correlated wavelet methods. In aspects, intrinsic contrast cross-correlated wavelet angiography may be calibrated to chemical contrast cross-correlated wavelet angiography.

In other aspects, the signal from intrinsic contrast may be cross-correlated with an external timing signal. The cross-correlated wavelet methods may use a cardiac signal as a cross-correland. For example, based on an external cardiac signal (for example, an electrocardiogram or time trace of a pulse oximeter), the acquisition of angiographic and cardiac signal data using intrinsic contrast at faster than cardiac rate as per the sampling theorem of Nyquist, Shannon, and Kotelnikov, and the operation upon these by complex-valued cross-correlated wavelet mathematics may be performed.

In other aspects, a measured or estimated cardiac frequency signal may be used wherein the shape of the cardiac curve is known/assumed, constant, and the interval between heartbeats is the same.

In other aspects, a calibration may be performed in which intrinsic contrast cross-correlated wavelet angiography is performed concurrently with conventional angiography with an injected intravascular contrast agent. For example, x-ray angiography may be performed, where a contrast agent is injected into the patient that attenuates the passage of x-rays, simultaneous with intrinsic contrast cross-correlated wavelet angiography. For example, optical contrast angiography may be performed, wherein a chemical agent such as ICG is injected into the patient to allow detection with an optical system having a near infrared filter. Intrinsic contrast wavelet angiography may be performed for a duration of time before and after the passage of the injected vascular optical contrast agent with which to calibrate intrinsic contrast wavelet angiography with intravascularly injected contrast wavelet angiography.

In aspects, a calibration step may be performed such that reconstructed cine images of spatiotemporal cardiac frequency phenomena using intrinsic contrast are compared to those obtained from conventional angiography obtained with intravascular administration of a chemical contrast agent. Imaging methods that may be used for the conventional chemical contrast angiography may include optical (including in the near infrared band) and/or fluoroscopic x-ray.

Initially, calibration chemical contrast angiography may be performed in all subjects that subsequently undergo intrinsic contrast cross-correlated wavelet angiography. However, in other aspects, the chemical contrast angiography portion of the process may be reduced and eventually eliminated by determining consistency between intrinsic contrast and conventional chemical contrast angiography.

The calibration embodiments listed herein include x-ray angiography and infrared optical angiography, but other calibrating angiography techniques may be employed, such as those employing magnetic resonance imaging and computed tomography. Optical coherence measurements (with Doppler effects) occurring at a sufficiently high speed for optical coherence image measurements to be acquired at faster than cardiac rate may also be used. In this example, data volumes from Doppler optical coherence tomography and from the optical coherence tomography capture of tissue motions may serve as a computational substrate for spatiotemporal reconstruction of cardiac frequency phenomena cross-correlated wavelet computational methods.

Any suitable imaging technique may be used for intrinsic contrast cross-correlated wavelet angiography including but not limited to optical, near infrared, ultrasound, Doppler (light or sound), and visible light. In some aspects, Doppler data may include a shift in wavelength relating to the movement of red blood cells towards or away from the imaging component. Doppler data may undergo preprocessing to account for this wavelength shift so that information pertaining to cardiac frequency is extracted and processed based on the techniques provided in the U.S. Pat. No. 10,123,761. For non-Doppler approaches, changes in tissue echogenicity may be a form of intrinsic contrast. For example, blood quantity in a given volume element may undergo changed in echogenicity as a function of cardiac frequency.

In an intrinsic contrast cross-correlated wavelet angiography calibration embodiment, chemical contrast is intravascularly injected and images are recorded at faster than cardiac rate. These cine images, both of the intrinsic contrast optical images and of the intravascularly injected chemical contrast angiographic images, are obtained in close temporal proximity or simultaneously, and may provide further amplification of the signal as opposed to either method alone. The intrinsic contrast and chemical contrast angiographic cine images may undergo cross-correlated wavelet reconstruction to reveal spatiotemporal cardiac frequency phenomena. A cross-correlated wavelet angiogram from chemical optical contrast wavelet angiography may be compared and contrasted to one reconstructed from intrinsic contrast wavelet optical angiography to calibrate the intrinsic contrast wavelet angiogram in terms of the underlying vascular physiology as revealed by the chemical contrast optical wavelet angiogram.

Cardiac frequency variation of intrinsic optical contrast, an optical manifestation of vascular phenomena that can be measured without intravascular administration of chemical contrast agent, is present in a variety of vascularized bodies. Optical intrinsic contrast includes but is not limited to tissue motion measured in visible wavelengths, heat emitted by blood flow and metabolism, and optical signatures of hemoglobin in its oxygenated and deoxygenated states. Intrinsic optical contrast may be measured in the visible and near infrared portions of the electromagnetic spectrum. The actions of the heart create cardiac frequency variation in intrinsic optical contrast, and cross-correlated wavelet spatiotemporal re-construction may be used to visualize the underlying cardiac frequency variation of the intrinsic contrast.

These techniques may be performed with a standard amount of chemical contrast, a reduced amount of chemical contrast, or with no chemical contrast, and unlike bolus approaches, the intrinsic contrast signal does not fade as a function of time. In the following examples, visual display of the operating field on a monitor display is optional.

FIG. 1A shows an example system 1000 for performing intrinsic contrast cross-correlated wavelet angiography. System 1000 comprises an operating microscope 3 configured to collect light from an operating field of view 1 of a patient and to divide the light into two pathways: a visible light pathway and a near infrared (NIR) light pathway. For example, light from an operating field 1 comprising a view of a patient may be collected by a lens 4 and directed to a beam splitter 2. In this example, the beam splitter splits the visible light into two pathways. One pathway comprising visible light may be directed by the beam splitter 2 into magnifying binoculars 1010 for an operating surgeon to view. Although magnifying binoculars are shown by way of example, the system may comprise any suitable viewing or display device, including a magnifying monocular, a display screen, etc. The other pathway may be directed by the beam splitter 2 to a camera 1030 (e.g., a charge coupled device (CCD) camera) via a NIR filter 1020. The camera 1030 may convert the received signal into a digitized form that may be provided to a computing system 1040. In an example embodiment, the CCD camera may capture images at a frame rate of 30 frames per second. In other example embodiments, the frame rate may range from 30 up to 240 frames per second. In still other example embodiments, the frame rate may range from 10-60 frames per second. In general, the camera will be sensitive to the wavelength of the cardiac frequency phenomena being studied (e.g., near infrared for cardiac frequency heat variation, hemoglobin peaks for arterial and venous blood volume variations, etc.). In example embodiments, the CCD camera may have an ISO of 50 up to 5400 or more. Preferably, the CCD camera will exhibit a linear signal response across a large dynamic range to capture cardiac frequency sinusoidal behavior. In example embodiments, the camera may have a minimum spatial resolution of 640×480 pixels at 1× to 10× spatial magnification power.

Computing system 1040 may process the received signal based on the intrinsic contrast cross-correlated wavelet angiography techniques provided herein to generate the intrinsic contrast angiogram on a display screen 1050. The operating microscope 3 may optionally be mounted on a mounting system 5 above the operating field of view. For example, mounting system 5 may include a pole 5a extending upwardly from a console holding computing system 1040, a rotatable boom 5b extending laterally from an upper end of the pole, and a microscope holder 5c suspended from an end of the boom. The operating microscope and mounting system described herein are shown by way of example only, and present techniques are suitable for any operating microscope and/or mounting system. In some aspects, visible light may also be provided to the CCD camera 1030, where it is processed for display on the display screen 1050. An external cardiac device 1060 (e.g., EKG, pulse oximeter, etc.) may be present for recording an external cardiac signal for cross-correlation. In some cases, an optional external light source 1070 may be present or, in the case of ultrasound, an ultrasound emitter 1075 may be present. It will be appreciated that intrinsic contrast angiograms obtained with the systems described herein may be displayed, stored in non-volatile memory, and/or printed by the computing system 1040.

FIG. 1B shows another embodiment of a system for performing intrinsic contrast cross-correlated wavelet angiography, in which intrinsic contrast techniques are performed using a video camera from a portable device (e.g., mobile phone, tablet, etc.). In this example, light from a diagnostic field of view 1110 is recorded by a portable device having a video recording feature (e.g., record images at faster than cardiac rate). An external cardiac device 1120 may also be present for recording a cross-correlation signal. The video images and cross correlation signal may be transmitted wirelessly (or through wire) to computer system 1140 to obtain the spatiotemporally reconstructed cardiac frequency signal and display the signal on display screen 1150. Alternatively, processing and/or display may be accomplished by the portable device 1130. In some cases, an optional external light source 1160 may be present, or in the case of ultrasound, an ultrasound emitter 1165 will be present.

The external cardiac signal, as a cross-correlation signal, provides a way to increase the signal to noise ratio, since signals arising from artifact sources will not vary as a function of cardiac frequency. Accordingly, the cross-correlation wavelet techniques of the U.S. Pat. No. 10,123,761 may be applied in the context of present techniques, with the external cardiac signal as the cross-correleand.

Figure 2:
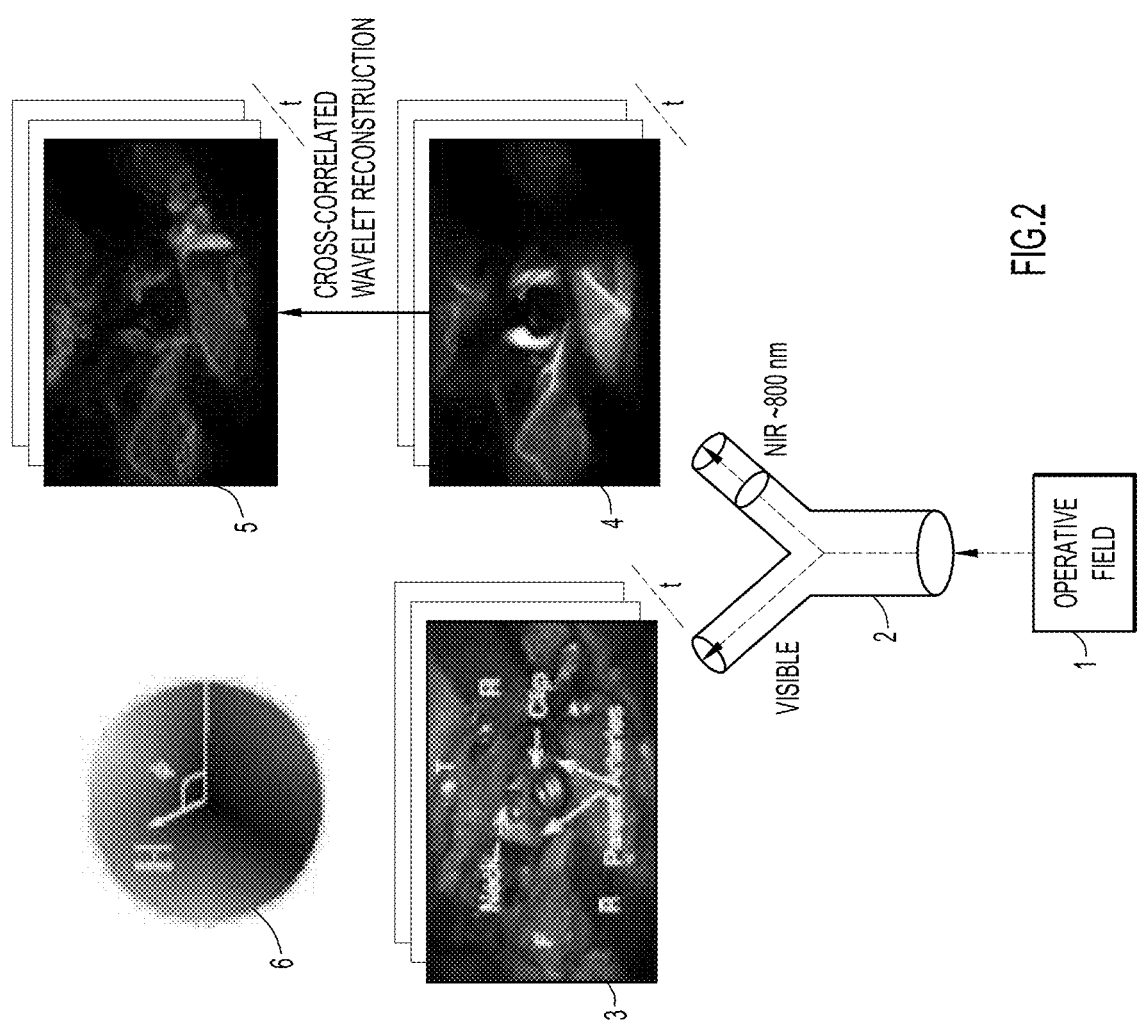
FIG. 2 shows visible and near infrared angiographic images obtained with the system of FIG. 1A using indocyanine green contrast administered as an intravascular contrast agent, according to aspects of the disclosure.

FIG. 2 shows an example of optical angiography with injection of an intravascular contrast agent. In this example, with the patient under anesthesia, an exposed human brain surface in the operative field 1 at clinical craniotomy is present. During a craniotomy, a clip is placed across the neck of a brain aneurysm to reduce the risk of repeat aneurysm rupture. The field is illuminated with near infrared light during the optical angiogram, and the intravascularly administered chemical contrast agent (e.g., indocyanine green (ICG), which fluoresces upon illumination in the near infrared spectrum) absorbs light at that wavelength and releases light in the near infrared wavelength range. The light from the exposed brain surface in the operative field 1 enters an operating microscope 1000 that has a beam splitter 2.

In this example, unfiltered light is recorded by a video or CCD camera 1030 to produce a visible video 3 recording of the angiographic field in the visible light spectrum. In this example, select features in the visible video 3 are annotated for clarity, including the frontal lobe (F) of the brain, the temporal lobe (T), the retractors (R), the aneurysm neck (Neck), the aneurysm clip (Clip), and the aneurysm parent arteries (Parent Arteries). The same beam splitter 2 sends light through a near infrared filter to a separate video or CCD camera and computer system that captures the near infrared video 4 that comprises the near infrared optical angiogram, with the near infrared signal generated from passing a chemical contrast bolus through the vasculature. The near infrared video 4 undergoes transformation, e.g., as taught by the U.S. Pat. No. 10,123,761, to produce a cross-correlated wavelet angiogram reconstruction 5 of the spatiotemporal phenomena occurring at cardiac frequency. Cardiac frequency phenomena in cross-correlated wavelet angiogram reconstruction 5 may be rendered pixel-wise as per a color model legend 6 comprising magnitude as brightness and phase as hue. With this color model, pixels without cardiac frequency activity are rendered as black and those with a large magnitude are rendered brightly. The phase of cardiac frequency activity varies circularly over the range $[-\pi, \pi]$ and is rendered with a periodic hue-based color map. Any suitable color model, e.g., grayscale, brightness, etc., may apply to any cross-correlated wavelet angiogram rendered in this application.

Figure 3:
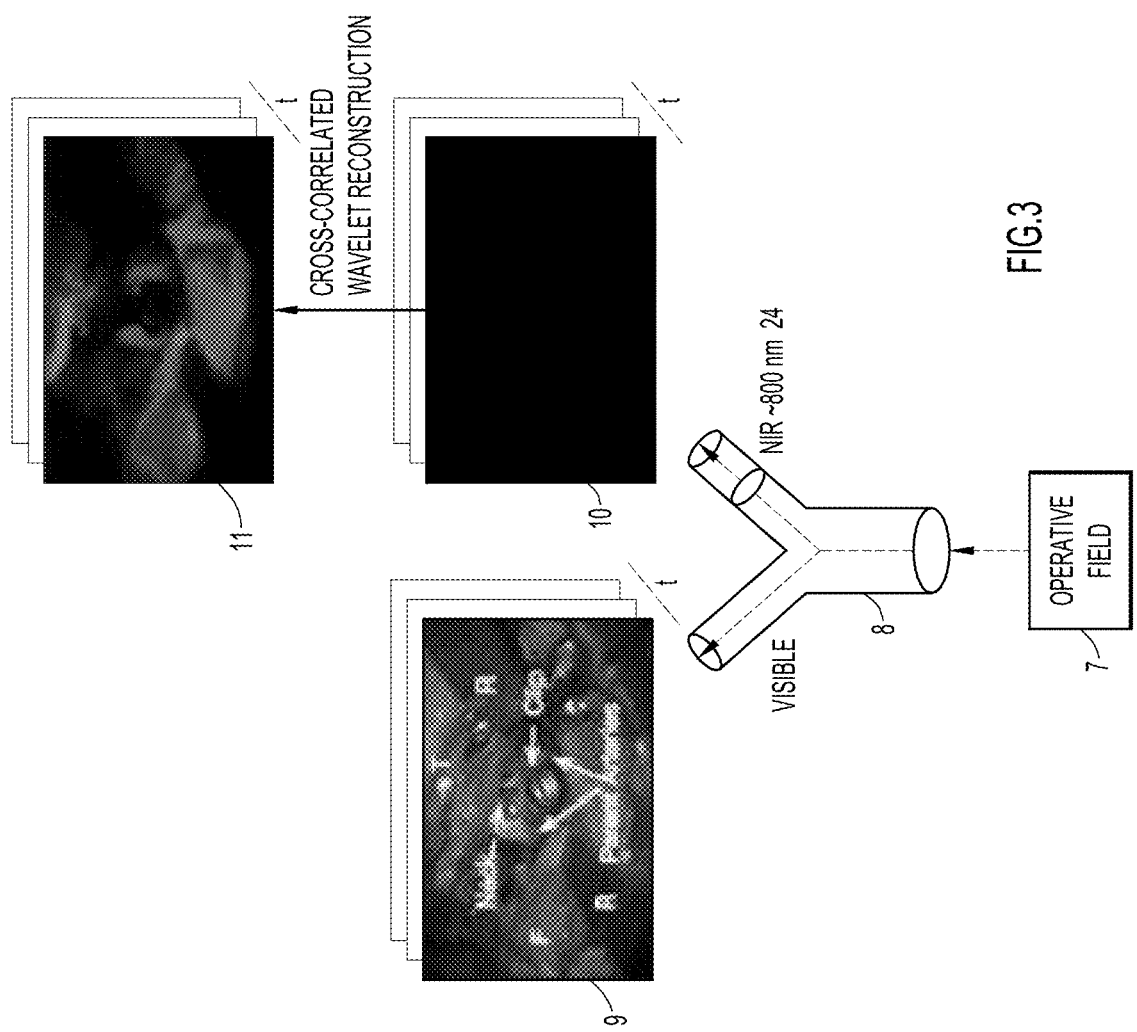
FIG. 3 shows visible and near infrared angiographic images obtained with the system of FIG. 1A using intrinsic contrast in the near infrared spectrum instead of an intravascularly administered chemical contrast agent, according to aspects of the disclosure.

FIG. 3 shows an example of optical angiography based on intrinsic contrast gathered in the near infrared optical spectrum rather than by injection of a chemical intravascular contrast agent. The elements in FIG. 3 are similar to those in FIG. 2 with the exception that cross-correlated wavelet angiogram reconstruction 11 is based on an angiogram with only intrinsic contrast. (Near infrared video 10 does not show a signal because near infrared chemical contrast agent was not intravascularly administered.) The cross-correlated wavelet angiography technique is able to resolve moving vascular pulse waves without the chemical contrast agent ICG. This effect may occur due to autofluorescence of tissue upon stimulation by near infrared light.

In this example, an exposed human brain surface in an operative field 7 at clinical craniotomy is present. Intrinsic contrast in the near infrared optical range is present due to a combination of infrared heat emission and reflectance of light by oxy-hemoglobin and deoxy-hemoglobin in the near infrared optical range. The light from the exposed brain surface operative field 7 enters an operating microscope 1000 that has a beam splitter 8. Unfiltered light is recorded by a video or CCD camera to generate, via a computing system 1040, a visible video 9 recording of the angiographic field in the visible light spectrum. Important features in the visible video 9 are annotated for clarity. The same beam splitter 8 sends light through a near infrared filter 24, for example, to another separate video recording device that captures the near infrared video 10 that comprises the intrinsic contrast near infrared optical angiogram. (In other aspects, the near infrared signal may be digitized and provided to a computer system 1040 for display onto a display screen.) The near infrared signal emitted by the exposed brain surface is less than the signal emitted from administration of intravascular chemical contrast agent ICG, and therefore, the near infrared video 10 images appear dark. However, even though the video appears dark, the signal from intrinsic contrast is present, and the pixels have organized cardiac frequency variation allowing the pulsing intrinsic contrast to be distinguished from the background signal. The spatiotemporal distribution of the cardiac frequency phenomena is detected and rendered into cine images as taught by the U.S. Pat. No. 10,123,761 by a cross-correlated wavelet angiogram reconstruction 11. This figure represents an example of the use of intrinsic contrast cross-correlated wavelet angiography.

As indicated previously, the wavelet processing techniques disclosed in the U.S. Pat. No. 10,123,761 may be applied to generate the intrinsic contrast angiogram. Without motion alias, the operations may comprise: receiving angiographic data consisting of n by m pixels by q frames into computer memory; reformatting the angiographic data with a processor to generate an n by m array of time signals, each q samples long; applying a complex valued wavelet transform by the processor to each pixel-wise time signal to generate an n by m array of wavelet transforms; filtering the pixel-wise wavelet transforms for cardiac frequency by the processor; performing on the pixel-wise wavelet transforms data an inverse wavelet transform by the processor into time domain and reformatting into q frames of n by m pixels; and rendering each frame as an image with a brightness hue color model to represent a complex datum in each pixel with the processor.

With motion alias and cross-correlation, the operations may comprise: applying a high frequency resolution wavelet transform by the processor to the angiographic time intensity curve; reformatting then angiographic data by the processor as an n by m array of time signals each of length q; performing a high temporal wavelet transformation by the processor on each pixel-wise time signal to generate an n by m array of high temporal resolution wavelet transforms; cross correlating in wavelet domain, each pixel-wise high temporal resolution wavelet transform by a single high frequency resolution wavelet transform of an overall angiographic time intensity curve by the processor; inverse wavelet transforming an n by m array of cross-correlated signals in wavelet domain to generate an n by m array of time domain time signals each of length q by the processor; and reformatting the n by m time signals of length a by the processor into q frames of n by m pixels, each complex valued. Additional details are available in the U.S. Pat. No. 10,123,761, which as previously mentioned, is incorporated by reference herein.

Figure 4:
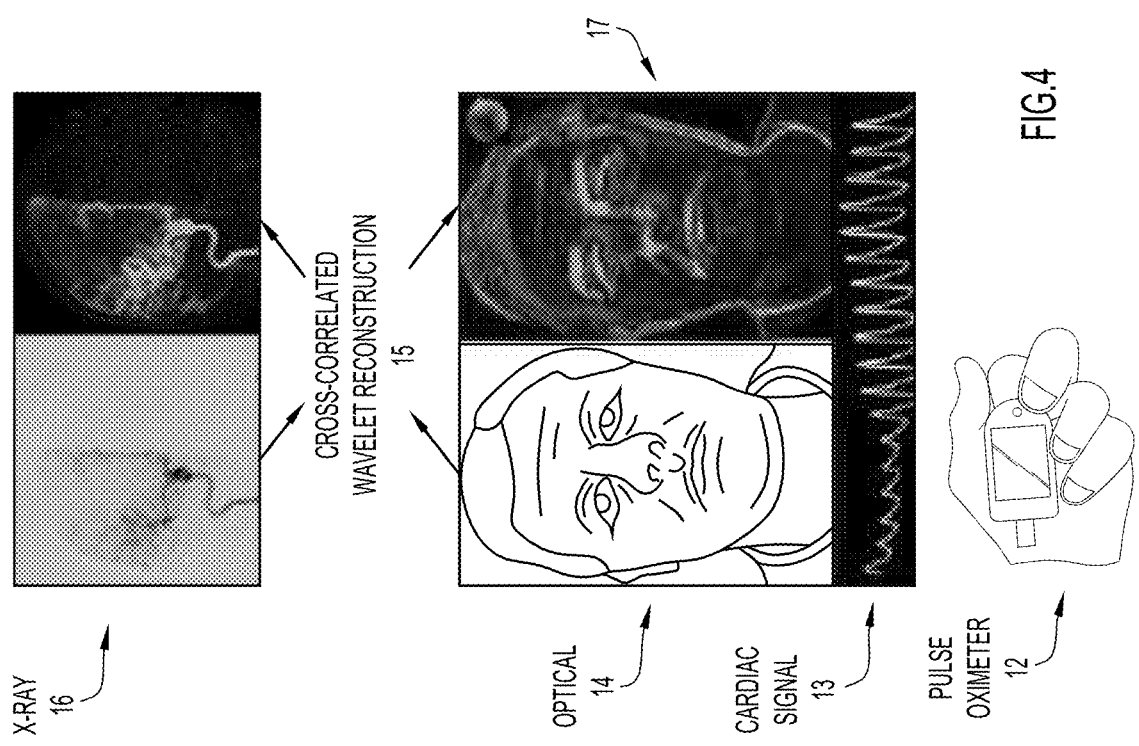
FIG. 4 compares intrinsic contrast optical angiography in visible wavelengths visualized within the vasculature of the skin and face to chemical intravascular contrast x-ray angiography of the cranium, according to aspects of the disclosure.

FIG. 4 shows an example of optical angiography of a human face based on intrinsic contrast obtained from the visible optical spectrum. Visible spectrum video cameras recording images of the human face show that the same cross-correlated wavelet algorithm can capture cardiac frequency via capturing small cardiac frequency motions in the head and facial tissues induced by the pulsatile kinetic energy of blood being pumped through the facial vasculature. Thus, cine images may be reconstructed of cardiac frequency variation using intrinsic contrast with cross-correlated wavelet mathematics applied to images acquired at faster than cardiac rate. Thus, quantitatively accurate measurement of cardiac frequency phenomena may be formed by using intrinsic contrast in optically imaged tissues.

In aspects, cross-correlated wavelet mathematics with an independently measured cardiac signal may be used to optically image the cardiac frequency phenomenon in those areas that partake in the circulatory system, including the skin. In this example, chemical contrast x-ray angiography of the cranium is used to calibrate and promote the interpretation of intrinsic contrast optical angiography of the same anatomic vicinity. For example, the subject wears a finger pulse oximeter 12 to generate non-invasively an external cardiac signal 13 to serve as the cross-correland by the cross-correlated wavelet reconstruction 15. Video footage 14 in the visible wavelengths is obtained of a human face to generate an intrinsic contrast optical face angiogram 17 based on cross-correlated wavelet reconstruction 15. After calculation by cross-correlated wavelet reconstruction 15, the reconstruction of cardiac frequency phenomena is rendered on the right hand side of intrinsic contrast optical face angiogram 17.

An x-ray angiogram of a human cranium 16 in anteroposterior projection with intravascularly administered chemical contrast into the right internal carotid artery is shown. As a calibration method, a conventional x-ray angiogram of intravascularly administered chemical contrast agent is shown on the left hand side of intravascular chemical contrast x-ray cranial angiogram and cross-correlated wavelet reconstruction 16. After processing by cross-correlated wavelet reconstruction 15, the reconstructed cardiac frequency phenomena is rendered on the right hand side of intravascular chemical contrast x-ray cranial angiogram and cross-correlated wavelet reconstruction 16. This figure shows intrinsic contrast optical angiography and cross-correlated wavelet reconstruction 14 and intravascular chemical contrast x-ray cranial angiogram and cross-correlated wavelet reconstruction 16 along with their cross-correlated wavelet reconstructions as two-dimensional images, but it is understated that these are example frames shown for illustration purposes from a cine sequence of images acquired at faster than cardiac rate.

The embodiments herein relate to x-ray angiography and infrared optical angiography, but other calibrating angiography techniques may be employed, such as those employing magnetic resonance imaging and computed tomography.

The examples provided herein demonstrate intrinsic contrast optical cross-correlated wavelet angiography of the brain surface and of the skin. These techniques may be applied to other vascularized organs such as the retina or other open surgical procedures.

Figure 5:
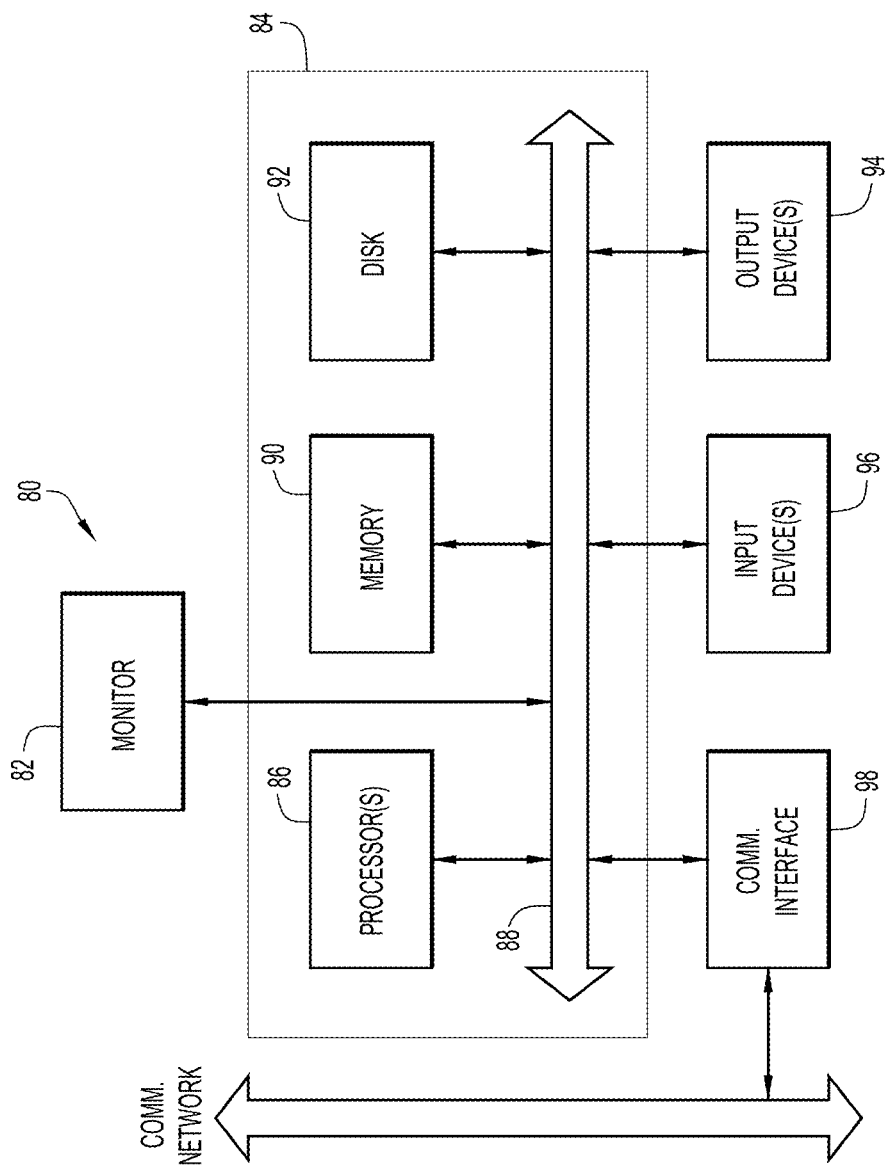
FIG. 5 is a block diagram of a computer system or information processing device that may be used with aspects of the disclosure.

Referring now to FIG. 5, a block diagram of a computer system or information processing device 80 (e.g., computer system 1040 in FIG. 1A or computer system 1140 in FIG. 1B) is illustrated that may be incorporated into an intrinsic contrast angiographic imaging system, such as the system 1000 in FIG. 1A or the system 1000 in FIG. 1B, to provide enhanced functionality or used as a standalone device for the extraction of cardiac frequency phenomena from angiographic data according to an embodiment of the present invention. In one embodiment, computer system 80 includes monitor or display 82, computer 84 (which includes processor(s) 86, bus subsystem 88, memory subsystem 90, and disk subsystem 92), user output devices 94, user input devices 96, and communications interface 98. Monitor 82 can include hardware and/or software elements configured to generate visual representations or displays of information. Some examples of monitor 82 may include familiar display devices, such as a television monitor, a cathode ray tube (CRT), a liquid crystal display (LCD), or the like. In some embodiments, monitor 82 may provide an input interface, such as incorporating touch screen technologies.

Computer 84 can include familiar computer components, such as one or more central processing units (CPUs), memories or storage devices, graphics processing units (GPUs), communication systems, interface cards, or the like. As shown in FIG. 5, computer 84 may include one or more processor(s) 86 that communicate with a number of peripheral devices via bus subsystem 88. Processor(s) 86 may include commercially available central processing units or the like. Bus subsystem 88 can include mechanisms for letting the various components and subsystems of computer 84 communicate with each other as intended. Although bus subsystem 88 is shown schematically as a single bus, alternative embodiments of the bus subsystem may utilize multiple bus subsystems. Peripheral devices that communicate with processor(s) 86 may include memory subsystem 90, disk subsystem 92, user output devices 94, user input devices 96, communications interface 98, or the like.

Memory subsystem 90 and disk subsystem 92 are examples of physical storage media configured to store data. Memory subsystem 90 may include a number of memories including random access memory (RAM) for volatile storage of program code, instructions, and data during program execution and read only memory (ROM) in which fixed program code, instructions, and data are stored. Disk subsystem 92 may include a number of file storage systems providing persistent (non-volatile) storage for programs and data. Other types of physical storage media include floppy disks, removable hard disks, optical storage media such as CD-ROMS, DVDs and bar codes, semiconductor memories such as flash memories, read-only-memories (ROMS), battery-backed volatile memories, networked storage devices, or the like. Memory subsystem 90 and disk subsystem 92 may be configured to store programming and data constructs that provide functionality or features of techniques discussed herein. Software code modules and/or processor instructions that when executed by processor(s) 86 implement or otherwise provide the functionality may be stored in memory subsystem 90 and disk subsystem 92.

User input devices 94 can include hardware and/or software elements configured to receive input from a user for processing by components of computer system 80. User input devices can include all possible types of devices and mechanisms for inputting information to computer system 84. These may include a keyboard, a keypad, a touch screen, a touch interface incorporated into a display, audio input devices such as microphones and voice recognition systems, and other types of input devices. In various embodiments, user input devices 94 can be embodied as a computer mouse, a trackball, a track pad, a joystick, a wireless remote, a drawing tablet, a voice command system, an eye tracking system, or the like. In some embodiments, user input devices 94 are configured to allow a user to select or otherwise interact with objects, icons, text, or the like that may appear on monitor 82 via a command, motions, or gestures, such as a click of a button or the like.

User output devices 96 can include hardware and/or software elements configured to output information to a user from components of computer system 80. User output devices can include all possible types of devices and mechanisms for outputting information from computer 84. These may include a display (e.g., monitor 82), a printer, a touch or force-feedback device, audio output devices, or the like.

Communications interface 98 can include hardware and/or software elements configured to provide unidirectional or bidirectional communication with other devices.

For example, communications interface 98 may provide an interface between computer 84 and other communication networks and devices, such as via an internet connection.

According to embodiments of the invention, it is recognized that, in addition to acquiring angiographic images, additional cardiac signals/data may be contemporaneously acquired to serve as a cross correlation target, for purposes of performing the spatiotemporal reconstruction of the vascular pulse waves based on the techniques provided herein. For example, the cardiac signals/data may serve as a reference cardiac signal for phase indexing pixels in the angiographic projections.

Figure 6:
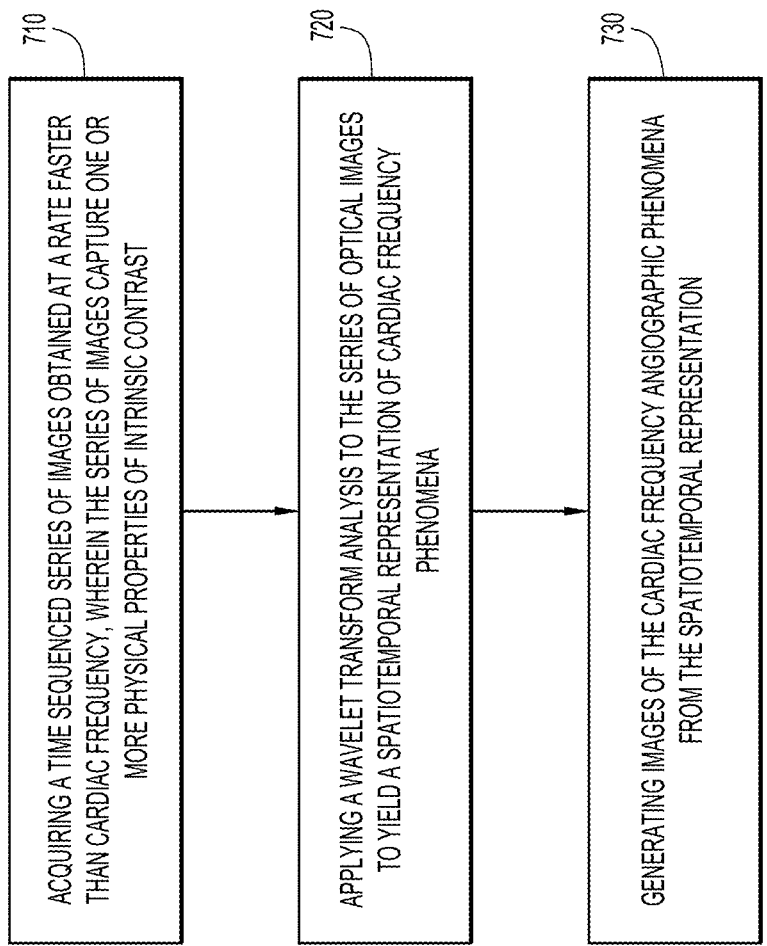
FIG. 6 is a flowchart showing techniques for intrinsic contrast optical angiography, according to aspects of the disclosure.

FIG. 6 shows high level operations of the techniques provided herein. At operation 710, a time sequenced series of images obtained at a rate faster than cardiac frequency is acquired, wherein the series of images capture one or more physical properties of intrinsic contrast. At operation 720, a wavelet transform analysis is applied to the series of optical images to yield a spatiotemporal representation of cardiac frequency phenomena. At operation 730, images of the cardiac frequency angiographic phenomena are generated from the spatiotemporal representation.

Beneficially, embodiments provided herein include a system, method, and computer readable media for spatiotemporally reconstructing cardiac frequency phenomena in angiographic data using intrinsic contrast. These techniques may be applied with a hardware system designed to obtain angiographic images, and in particular an angiographic system, to obtain images for a patient. These techniques provide an improvement in the art over existing angiographic approaches, namely, allowing the spatiotemporal cardiac frequency phenomenon to be visualized without chemical contrast. Additionally, this signal does not decay or fade over time, allowing ongoing visualization of spatiotemporal cardiac frequency phenomena, which may be helpful during surgical procedures or ongoing monitoring of patient status.

The cardiac frequency variation comprises a source of information in the intrinsic contrast that increases the signal to noise ratio upon spatiotemporal cross-correlated wavelet reconstruction of the cardiac frequency variation of the intrinsic contrast. Furthermore, embodiments presented herein exploit the phenomenon of arteriovenous phase locking to distinguish in cine images the arterial from venous circulatory sub-systems by analysis of their consistent cardiac frequency phase relations.

These techniques may be used to screen for medical abnormalities, such as blocked arteries within limbs or the head, which could select patients for further screening. In aspects, multiple optical recordings may be obtained and different positions of a body may be screened for abnormalities (e.g., between the head and leg, arm and leg, etc.). Additionally, present techniques may be applied to performing optical retinal angiography without a contrast agent. In some aspects, disruption of cardiac frequency phenomenon may occur prior to changes in pathology, allowing present techniques to diagnose medical conditions earlier than with presently available technology.

Present techniques provide improvements in the field of medical technology and medical imaging. These techniques may be used to detect circulatory abnormalities with reduced or no contrast. Additionally, techniques may be visible with processing of video technology. By detecting changes in cardiac frequency activity, patients may quickly be screened and further testing may be performed as indicated. Additionally, intrinsic contrast angiograms may be obtained over a period of time, with the first intrinsic contrast angiogram functioning as a baseline. Changes in the baseline over time may indicate development of an underlying circulatory or cardiac disorder.

These inventive techniques may improve operating or surgical imaging systems designed to be used in a surgical setting, diagnostic imaging systems, and other types of optical imaging systems by making it possible for such systems to extract and display information about cardiac frequency phenomena using intrinsic contrast.

These techniques may offer further advantages for critically ill patients or intraoperative patients where intravenous access is available as a matter of course. For example, the need to coordinate intravenous contrast with optical capture dominates the procedure and causes interruption of other medical steps. For the patient otherwise without intravenous access, this approach may spare the discomfort and inconvenience of having an intravenous injection.

Rapid or transient phenomena that are medically meaningful may occur without warning, such that an injected contrast bolus may not be circulating at a given moment to allow imaging and analysis of the phenomena. With intrinsic contrast, since cardiac frequency phenomena are always available in the living patient, one can analyze extemporaneously, post-hoc, or continuously, the cardiac frequency phenomena in images acquired at faster than cardiac rate.

In other aspects, multiple type of inputs may be obtained (e.g., light, near infrared, thermal heat, sound, etc.) and processed, and the resulting outputs combined to boost cardiac frequency detection as compared to a single input.

It will thus be seen that the objects set forth above, among those made apparent from the preceding description, are efficiently attained and, because certain changes may be made in carrying out the above method and in the construction(s) set forth without departing from the spirit and scope of the invention, it is intended that all matter contained in the above description and shown in the accompanying drawings shall be interpreted as illustrative and not in a limiting sense.

It is also to be understood that the following claims are intended to cover all of the generic and specific features of the invention herein described and all statements of the scope of the invention which, as a matter of language, might be said to fall there-between.

The techniques provided herein have been described in terms of the preferred embodiment, and it is recognized that equivalents, alternatives, and modifications, aside from those expressly stated, are possible and within the scope of the appending claims.

What is claimed:

1. A method of extracting cardiac frequency phenomena from a series of optical images obtained by an optical system at faster than cardiac frequency comprising:
   acquiring a time sequenced series of optical images of a patient obtained at a rate faster than cardiac frequency, wherein the time sequenced series of optical images capture one or more physical properties of intrinsic contrast;
   acquiring a cross-correland signal from the patient;
   applying a cross-correlated wavelet transform analysis to the time sequenced series of optical images to yield a spatiotemporal representation of cardiac frequency phenomena, wherein the cross-correlated wavelet transform analysis comprises:
      performing a wavelet transform on the time sequenced series of optical images to obtain a wavelet transformed signal;
      cross-correlating the wavelet transformed signal with the cross-correland signal to obtain a cross-correlated signal;
      filtering the cross-correlated signal at cardiac frequency to obtain a filtered signal, and
      performing an inverse wavelet transform on the filtered signal to obtain a spatiotemporal representation of the time sequenced series of optical images; and
      generating images of the cardiac frequency phenomena from the spatiotemporal representation.

2. The method of claim 1, further comprising displaying the spatiotemporal representation in one or more reconstructed images.

3. The method of claim 1, further comprising obtaining a contemporaneously measured cardiac signal and cross-correlating the contemporaneously measured cardiac signal with the wavelet transformed signal.

4. The method of claim 1, wherein the series of optical images are obtained by optical microscopy, near-infrared microscopy, ultrasound, or Doppler technology.

5. The method of claim 1, wherein the series of optical images are obtained from imaging a body with a vascular structure.

6. The method of claim 1, wherein the intrinsic contrast comprises thermal radiation, optical reflection, or autofluorescence.

7. The method of claim 1, wherein the images of the cardiac frequency phenomena are provided as a cine video sequence.

8. The method of claim 1, further comprising:
   acquiring a second time sequenced series of images with intravenously injected chemical contrast and generating a second spatiotemporal representation of the images obtained from the intravenously injected chemical contrast;
   pairing the spatiotemporal representation of the time sequenced series of optical images with the second spatiotemporal representation of the images obtained from the intravenously injected chemical contrast; and
   calibrating the spatiotemporal representation of the time sequenced series of optical images based on the pairing.

9. An optical system for extracting cardiac frequency phenomena obtained at a rate faster than cardiac frequency, the system comprising:
   one or more computer processors;

one or more computer readable storage media; and
program instructions stored on the one or more computer readable storage media for execution by at least one of the one or more computer processors, the program instructions comprising instructions to:
acquire a time sequenced series of optical images of a patient obtained at a rate faster than cardiac frequency, wherein the time sequenced series of optical images capture one or more physical properties of intrinsic contrast;
acquire a cross-correland signal from the patient;
apply a cross-correlated wavelet transform analysis to the time sequenced series of optical images to yield a spatiotemporal representation of cardiac frequency phenomena, wherein the cross-correlated wavelet transform analysis comprises:
performing a wavelet transform on the time sequenced series of optical images to obtain a wavelet transformed signal;
cross-correlating the wavelet transformed signal with the cross-correland signal to obtain a cross-correlated signal;
filtering the cross-correlated signal at cardiac frequency to obtain a filtered signal, and
performing an inverse wavelet transform on the filtered signal to obtain a spatiotemporal representation of the time sequenced series of optical images; and
generate images of the cardiac frequency phenomena from the spatiotemporal representation.

10. The system of claim 9, wherein the program instructions further comprise instructions to:
display the spatiotemporal representation in one or more reconstructed images.

11. The system of claim 9, wherein the program instructions further comprise instructions to:
obtain a contemporaneously measured cardiac signal and cross-correlate the contemporaneously measured cardiac signal with the wavelet transformed signal.

12. The system of claim 9, wherein the series of optical images are obtained by optical microscopy, near-infrared microscopy, ultrasound, or Doppler technology.

13. The system of claim 9, wherein the series of optical images are obtained from imaging a body with a vascular structure.

14. The system of claim 9, wherein the intrinsic contrast comprises thermal radiation, optical reflection, or autofluorescence.

15. The system of claim 9, wherein the images of the cardiac frequency are provided as a cine video sequence.

16. The system of claim 9, wherein the program instructions further comprise instructions to:
acquire a second time sequenced series of images with intravenously injected chemical contrast and generate a second spatiotemporal representation of the images obtained from the intravenously injected chemical contrast;
pair the spatiotemporal representation of the time sequenced series of optical images with the second spatiotemporal representation of the images obtained from the intravenously injected chemical contrast; and
calibrate the spatiotemporal representation of the time sequenced series of optical images based on the pairing.

17. A computer program product for extracting cardiac frequency phenomena obtained at a rate faster than cardiac frequency, the computer program product comprising one or more non-transitory computer readable storage media collectively having program instructions embodied therewith, the program instructions executable by a computer to cause the computer to:
acquire a time sequenced series of optical images from a patient obtained at a rate faster than cardiac frequency, wherein the time sequenced series of optical images capture one or more physical properties of intrinsic contrast;
acquire a cross-correland signal from the patient;
apply a cross-correlated wavelet transform analysis to the time sequenced series of optical images to yield a spatiotemporal representation of cardiac frequency phenomena, wherein the cross-correlated wavelet transform analysis comprises:
performing a wavelet transform on the time sequenced series of optical images to obtain a wavelet transformed signal;
cross-correlating the wavelet transformed signal with the cross-correland signal to obtain a cross-correlated signal;
filtering the cross-correlated signal at cardiac frequency to obtain a filtered signal; and
performing an inverse wavelet transform on the filtered signal to obtain a spatiotemporal representation of the time sequenced series of optical images; and
generate images of the cardiac frequency phenomena from the spatiotemporal representation.

18. The computer program product of claim 17, wherein the program instructions further comprise instructions to:
display the spatiotemporal representation of cardiac frequency angiographic phenomena in one or more reconstructed images.

19. The computer program product of claim 17, wherein the program instructions further comprise instructions to:
obtain a contemporaneously measured cardiac signal and cross-correlate the contemporaneously measured cardiac signal with the wavelet transformed signal.

20. The computer program product of claim 17, wherein the program instructions further comprise instructions to:
acquire a second time sequenced series of images with intravenously injected chemical contrast and generate a second spatiotemporal representation of the images obtained from the intravenously injected chemical contrast;
pair the spatiotemporal representation of the time sequenced series of optical images with the second spatiotemporal representation of the images obtained from the intravenously injected chemical contrast; and
calibrate the spatiotemporal representation of the time sequenced series of optical images based on the pairing.

* * * * *